United States Patent
Roussis et al.

(10) Patent No.: US 9,200,208 B2
(45) Date of Patent: *Dec. 1, 2015

(54) COMPOSITIONS OF MATTER COMPRISING EXTRACTED ALGAE OIL

(75) Inventors: Stilianos G. Roussis, Vista, CA (US); Richard J. Cranford, San Diego, CA (US)

(73) Assignee: SAPPHIRE ENERGY, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/237,537

(22) PCT Filed: Aug. 9, 2012

(86) PCT No.: PCT/US2012/050189
§ 371 (c)(1),
(2), (4) Date: Mar. 17, 2014

(87) PCT Pub. No.: WO2013/023086
PCT Pub. Date: Feb. 14, 2013

(65) Prior Publication Data
US 2014/0249338 A1    Sep. 4, 2014

Related U.S. Application Data

(60) Provisional application No. 61/521,687, filed on Aug. 9, 2011.

(51) Int. Cl.
*C10G 3/00* (2006.01)
*A23D 9/00* (2006.01)
(Continued)

(52) U.S. Cl.
CPC .. *C10G 3/00* (2013.01); *A23D 9/00* (2013.01); *A23D 9/007* (2013.01); *C10G 3/42* (2013.01);
(Continued)

(58) Field of Classification Search
CPC ........................................................ C10G 3/00
USPC .................................... 585/240; 44/307, 308
See application file for complete search history.

(56) References Cited

U.S. PATENT DOCUMENTS

| 4,992,605 A | 2/1991 | Craig et al. |
| 5,939,229 A | 8/1999 | Robbins |

(Continued)

FOREIGN PATENT DOCUMENTS

| BR | PI0805091 A2 | 9/2010 |
| WO | 2007/012643 A1 | 2/2007 |

(Continued)

OTHER PUBLICATIONS

Fu et al., "Catalytic hydrothermal deoxygenation of palmitic acid." Energy Environ. Sci., 2010, vol. 3, pp. 311-317.

(Continued)

*Primary Examiner* — Ellen McAvoy
(74) *Attorney, Agent, or Firm* — Sapphire Energy, Inc.

(57) ABSTRACT

Crude algae oils produced by practical extraction techniques comprise a wide range of molecular species that can be characterized by advanced analytical techniques. The algae oils comprise a complex mixture of a large number of molecules having varying sizes and therefore varying boiling points, and comprise high nitrogen, oxygen, and fatty acid content, but low sulfur, saturated hydrocarbons, and triglyceride content. Hydrogen/carbon molar ratios are typically greater than 1.6. The wide range of molecular species in the crude algae oils, while unusual compared to conventional refinery feed stocks and vegetable oils, may be upgraded into fuels by conventional refining approaches such as hydrotreating and thermal treatment. Unusual behavior of the algae oils in thermal processing and/or hydrotreatment may provide a high quality product slate, with the flexibility to adjust the product slate due to enhanced cracking behavior exhibited by these algae oils.

15 Claims, 15 Drawing Sheets

(51) Int. Cl.
*A23D 9/007* (2006.01)
*C12P 7/64* (2006.01)

(52) U.S. Cl.
CPC .......... *C10G 3/50* (2013.01); *C10G 2300/1014* (2013.01); *C12P 7/6409* (2013.01); *C12P 7/6436* (2013.01)

(56) References Cited

U.S. PATENT DOCUMENTS

| | | | |
|---|---|---|---|
| 6,166,230 | A | 12/2000 | Bijl et al. |
| 6,399,803 | B1 | 6/2002 | Corley et al. |
| 7,425,412 | B2 | 9/2008 | Lo et al. |
| 7,491,858 | B2 | 2/2009 | Murzin et al. |
| 8,192,628 | B2 | 6/2012 | Cranford et al. |
| 2008/0155888 | A1 | 7/2008 | Vick et al. |
| 2008/0305445 | A1 | 12/2008 | Roberts et al. |
| 2008/0308457 | A1 | 12/2008 | Dindi et al. |
| 2009/0069610 | A1 | 3/2009 | Roberts, IV et al. |
| 2009/0126260 | A1 | 5/2009 | Aravanis et al. |
| 2009/0266743 | A1 | 10/2009 | Yao et al. |
| 2009/0298159 | A1 | 12/2009 | Wu et al. |
| 2010/0050502 | A1 | 3/2010 | Wu et al. |
| 2010/0239712 | A1 | 9/2010 | Brooks et al. |
| 2010/0297749 | A1 | 11/2010 | Aravanis et al. |
| 2011/0092725 | A1 | 4/2011 | Jones |
| 2012/0282662 | A1* | 11/2012 | Kale .......................... 435/134 |
| 2012/0283496 | A1* | 11/2012 | Kale .......................... 585/310 |
| 2013/0115664 | A1* | 5/2013 | Khanna et al. ................ 435/134 |
| 2013/0164798 | A1* | 6/2013 | Vanhercke et al. ............ 435/134 |
| 2013/0295268 | A1* | 11/2013 | Day et al. ..................... 426/603 |
| 2013/0296591 | A1* | 11/2013 | Day et al. ..................... 554/124 |
| 2014/0093945 | A1* | 4/2014 | Dillon et al. .................. 435/271 |
| 2014/0113363 | A1* | 4/2014 | Oyler ......................... 435/294.1 |
| 2014/0249342 | A1* | 9/2014 | Franklin et al. ............... 585/310 |
| 2014/0305031 | A1* | 10/2014 | Day et al. ......................... 44/388 |

FOREIGN PATENT DOCUMENTS

| | | |
|---|---|---|
| WO | WO 2007/027955 A2 | 3/2007 |
| WO | WO 2008/103204 A2 | 8/2008 |
| WO | WO 2010/124030 A1 | 10/2010 |
| WO | WO 2011/025616 A2 | 3/2011 |

OTHER PUBLICATIONS

Peterson et al., "Thermochemcial biofuel production in hydrothermal media: A review of sub- and supercritical water technologies." Energy & Environmental Science, 2008, vol. 1, pp. 32-65.

Shuping et al., "Production and characterization of bio-oil from hydrothermal liquefaction of microalgae Dunaliella tertiolecta cake." Energy, 2010, vol. 35, pp. 5406-5411.

Sims. Waste Not. Biomassmagazine.com. Oct. 2011. pp. 1-2.

Valdez et al., "Characterization of product fractions for hydrothermal liquefaction of *Nannochloropsis* sp and the influence of solvents." Energy & Fuels, 2011, vol. 25, pp. 3235-3243.

Brown et al., "Hydrothermal liquefaction and gasification of *Nannochloropsis* sp." Energy and Fuels, 2010, vol. 24, pp. 3639-3646.

Ross et al., "Hydrothermal processing of microalgae using alkali and organic acids." Fuel, 2010, vol. 89, pp. 2234-2243.

Extended European Search Report in EP12821703.1, dated Mar. 25, 2015 in the name of Sapphire Energy, Inc.

Haicduc, J. Appl. Pychol. (2009). 21(5):529-541.

* cited by examiner

COMPOSITIONS OF MATTER COMPRISING EXTRACTED ALGAE OIL

CROSS REFERENCE TO RELATED APPLICATION

This application claims the benefit of U.S. Provisional Application No. 61/521,687, filed Aug. 9, 2011, entitled COMPOSITIONS OF MATTER OF EXTRACTED ALGAE OIL AND METHODS OF MAKING SAME, which is herein incorporated by reference in its entirety for all purposes.

BACKGROUND

The disclosure relates to renewable oil compositions of matter extracted from biomass, and/or methods and/or apparatus for obtaining the compositions of matter. More specifically, certain embodiments of the disclosure relate to compositions of matter comprising extracted algae oils that may have high nitrogen, oxygen, and fatty acid content, high hydrogen to carbon ratios, and low saturated hydrocarbon content. Certain embodiments of the extracted algae oils contain little sulfur and little or no triglycerides. These algae oil characteristics are unusual in comparison to conventional fossil petroleum crude oils and to vegetable oils that have been studied in recent years as candidates for production of renewable fuels. As disclosed in other of the Applicants' patent applications, and briefly described herein, upgrading embodiments of the novel algae oils have been accomplished by thermal treatment, hydrotreatment, and/or deoxygenation at operating conditions compatible with existing petroleum refinery process units. The upgrading has produced advantageous results that are unusual compared to fossil and/or vegetable feed stocks. The unusual characteristics of the algae oils, therefore, are expected to make the algae oils good candidates for upgrading and co-processing in conventional petroleum refineries.

Increasing energy demands and decreasing fossil petroleum reserves require that renewable energy sources be developed and improved. Meeting this need with renewable oils obtained from biomass will be more feasible and economical if the renewable oil can be treated efficiently in existing petroleum refineries or at least with conventional petroleum refining process designs. This way, decades of research and development and capital investment may be utilized to process and upgrade refinery-compatible renewable oils or blends of renewable oils and fossil oils.

Long lists of renewable oils have been proposed in early discussions of alternative fuels, and long lists of conventional refinery processes have been proposed for upgrading the renewable oils. In these early discussions, algae oils have been grouped with vegetable oils as candidates for processing by conventional petroleum refinery units, but very little information about algae oil composition has been disclosed or discussed, except that algae oil comprises hetero-atoms. In patent literature, algae oils are typically grouped with vegetable oils as high-triglyceride oils and the assumption has been made that these oils can be upgraded in conventional refineries, but little confirmatory data or detail has been disclosed. Refiners have expressed concern that high-triglyceride and/or high hetero-atom containing oils are incompatible with their equipment and process schemes and are not characterized and understood sufficiently to be fed to their refineries.

There is a need, therefore, for algae oil compositions of matter that are compatible with conventional petroleum refineries, and a need for detailed characterization of the algae oils that can guide selection of flowscheme, catalyst, and/or operating conditions in conventional refinery units. Various embodiments of the disclosure meet these needs, and comprise extracted algae oils that have unique compositions compared to fossil petroleum and vegetable oils. Further, the composition of the unique algae oils has been studied and reported in this disclosure, laying a foundation for informed selection of processes and conditions to upgrade the algae oils for use as renewable fuels.

SUMMARY OF THE DISCLOSURE

The novel compositions of matter comprise oil extracted from biomass, wherein the oil is low in saturated hydrocarbon content, and high in oxygen, nitrogen, and fatty acid content. In most embodiments, the extracted oil is low in sulfur and triglyceride content. The disclosure may also comprise equipment and/or methods for extracting or processing the oil.

Certain oils according to the disclosure are extracted from algae biomass and include a wide range of compound types, which is unexpected in view of vegetable oils (that are mainly triglycerides) and petroleum fractions of similar boiling range (that are mainly saturated hydrocarbons and aromatics). Certain oils according to the disclosure have a boiling range of approximately 300-1300 degrees Fahrenheit (F) true boiling point (approximately 150-700 degrees Celsius (C)), and comprise less than 10 area % saturated hydrocarbons, less than 10 area % aromatics, and greater than 15 area % fatty acids, as measured by calculating percentages of peak area as measured by HT GC-MS. Some algae strains result in extracted algae oil having greater than 5 area % sterols. Also unusual compared to the vegetable oils and petroleum fractions are hydrogen to carbon ratios of greater than 1.5 and typically greater than 1.6, and oxygen content greater than 5 wt % and nitrogen content greater than 3 wt % as measured by elemental analysis. Many oils according to the disclosure have little or no triglyceride content. These highly-aliphatic (non-aromatic), hydrogen- and oxygen-rich, high-fatty-acid oils are polar, as a result of comprising considerable amounts of polar compounds. For example, polar compounds contained in many embodiments of the extracted algae oil include fatty acids, sterols, nitrogen compounds (nitrogen-containing compounds), oxygen compounds (oxygen-containing compounds), amides, and nitriles.

Certain embodiments of the novel composition of matter are extracted from biomass using hydrothermal extraction methods. The hydrothermal extraction methods typically include heating and acidifying of a biomass- and -water composition, followed by solvent extraction to obtain an oleaginous composition. An exemplary biomass is algae biomass, with the oleaginous composition being crude algae oil, as illustrated and described in the examples of the Detailed Description. Tables, and Figures. While these examples disclose specific compositions, means, and methods, it should be understood that other embodiments are included in the broad scope of the disclosure.

Provided herein are oleaginous compositions comprising an algal oil extracted from biomass comprising a non-vascular photosynthetic organism, wherein the algal oil comprises: an area percent of saturated hydrocarbons from about 1.2 to about 3.0; an area percent of unsaturated hydrocarbons from about 5.8 to about 9.9; an area percent of aromatics from about 2.5 to about 3.7; an area percent of Nitrogen compounds from about 4.2 to about 8.1; an area percent of amides from about 1.1 to about 13.7; and an area percent of Oxygen compounds from about 1.9 to about 6.9. In some embodiments, the algal oil further comprises an area percent of fatty acids and/or fatty acid esters from about 22.7 to about 35.5. In other embodiments, the algal oil further comprises an area percent of sterols and/or steroids from about 3.4 to about 4.0. In one embodiment, the non-vascular photosynthetic organism is a microalga. In other embodiments, the microalga is a *Dunaliella* species, a *Scenedesmus* species, or a *Spirulina* species. In yet another embodiment, the biomass is substantially photosynthetic algae and the oil is substantially algal oil. In other embodiments, a fraction of the algal oil is selected from the group consisting of a naphtha fraction, a kerosene fraction, a jet fuel fraction, a distillate fraction, a diesel fraction, a gas oil fraction, a light gas oil fraction, a heavy gas oil fraction, and a residue fraction. In yet other embodiments, the fraction of algal oil has a boiling range of a fraction produced in a petroleum refinery crude distillation tower. In other embodiments, the fraction of algal oil is selected from a group consisting of: butanes to about 430 degrees F (naphtha), about 430-about 650 degrees F (distillate), and about 650-about 1000 degrees F (gas oil).

Also provided herein are oleaginous compositions comprising an algal oil extracted from biomass comprising a non-vascular photosynthetic organism, wherein the algal oil comprises: from about 77.6 to about 78.0 weight percent Carbon; from about 10.2 to about 10.6 weight percent Hydrogen; and from about 3.0 to about 5.3 weight percent Nitrogen. In some embodiments, the algal oil further comprises from about 1.2 to about 1.4 weight percent Sulfur. In other embodiments, the algal oil further comprises from about 5.1 to about 7.2 weight percent Oxygen by difference. In some embodiments, the algal oil has a Hydrogen to Carbon ratio is about 1.63, is above 1.6, or is from about 1.6 to about 2.1. In one embodiment, the non-vascular photosynthetic organism is a microalga. In other embodiments, the microalga is a *Dunaliella* species, a *Scenedesmus* species, or a *Spirulina* species. In one embodiment, the biomass is substantially photosynthetic algae and the oil is substantially algal oil. In other embodiments, a fraction of the algal oil is selected from the group consisting of a naphtha fraction, a kerosene fraction, a jet fuel fraction, a distillate fraction, a diesel fraction, a gas oil fraction, a light gas oil fraction, a heavy gas oil fraction, and a residue fraction. In yet other embodiments, the fraction of algal oil has a boiling range of a fraction produced in a petroleum refinery crude distillation tower. In other embodiments, the fraction of algal oil is selected from a group consisting of: butanes to about 430 degrees F (naphtha), about 430-about 650 degrees F (distillate), and about 650-about 1000 degrees F (gas oil).

Provided herein are oleaginous compositions comprising an algal oil extracted from biomass comprising a non-vascular photosynthetic organism, wherein the algal oil comprises: a) less than or equal to 10 area % saturated hydrocarbons, from about 0.1 to about 5 area % saturated hydrocarbons, or from about 0.1 to about 3 area % saturated hydrocarbons; and/or b) greater than or equal to 5 area % Oxygen, or from about 6 to about 10 area % Oxygen; and/or c) greater than or equal to 3 area % Nitrogen, or from about 3.5 to about 6 area % Nitrogen; and/or d) greater than or equal to 15 area % fatty acids and/or fatty acid esters, from about 15 to about 60 area % fatty acids and/or fatty acid esters, or from about 15 to about 40 area % fatty acids and/or fatty acid esters; and/or e) less than or equal to 2 area % Sulfur, or less than or equal to 1.5 area % Sulfur; and/or f) less than or equal to 1 area % triglycerides, or less than or equal to 0.05 area % triglycerides; and/or g) a Hydrogen to Carbon molar ratio of greater than or equal to 1.6, or a Hydrogen to Carbon molar ratio of from about 1.6 to about 2.1; and/or h) less than or equal to 10 area % aromatics, from about 0.1 to about 5 area % aromatics, or from about 0.1 to about 3 area % aromatics; and/or i) from about 0.1 to about 2 area % nitriles; and/or j) from about 1 to about 15 area % amides; and/or k) from about 1 to about 10 area % Nitrogen compounds; and/or l) from about 1 to about 15 area % Oxygen compounds; and/or m) greater than or equal to 5 area % sterols and/or steroids, or from about 8 to about 15 area % sterols and/or steroids. In some embodiments, the algal oil comprises any 7 or more of a) through m). In other embodiments, the algal oil comprises any ten or more of a) through m). In one embodiment, the non-vascular photosynthetic organism is a microalga. In some embodiments, the microalga is a *Dunaliella* species, a *Scenedesmus* species, or a *Spirulina* species. In an embodiment, the biomass is substantially photosynthetic algae and the oil is substantially algal oil. In other embodiments, a fraction of the algal oil is selected from the group consisting of a naphtha fraction, a kerosene fraction, a jet fuel fraction, a distillate fraction, a diesel fraction, a gas oil fraction, a light gas oil fraction, a heavy gas oil fraction, and a residue fraction. In yet other embodiments, the fraction of algal oil has a boiling range of a fraction produced in a petroleum refinery crude distillation tower. In other embodiments, the fraction of algal oil is selected from a group consisting of: butanes to about 430 degrees F (naphtha), about 430-about 650 degrees F (distillate), and about 650-about 1000 degrees F (gas oil).

Also provided herein are oleaginous composition comprising an algal oil extracted from biomass comprising a non-vascular photosynthetic organism, made by a method comprising: a) obtaining the biomass; b) hydrothermally treating the biomass at a temperature from about 260 degrees Celsius to about 300 degrees Celsius, and holding the temperature from zero to about 240 minutes; c) acidifying the biomass; and d) extracting the composition from the biomass, wherein the algal oil comprises: an area percent of saturated hydrocarbons from about 1.2 to about 3.0; an area percent of unsaturated hydrocarbons from about 5.8 to about 9.9; an area percent of aromatics from about 2.5 to about 3.7; an area percent of Nitrogen compounds from about 4.2 to about 8.1; an area percent of amides from about 1.1 to about 13.7; and an area percent of Oxygen compounds from about 1.9 to about 6.9. In some embodiments, the algal oil further comprises an area percent of fatty acids and/or fatty acid esters from about 22.7 to about 35.5. In other embodiments, the algal oil further comprises an area percent of sterols and/or steroids from about 3.4 to about 4.0. In one embodiment, the non-vascular photosynthetic organism is a microalga. In other embodiments, the microalga is a *Dunaliella* species, a *Scenedesmus* species, or a *Spirulina* species. In one embodiment, the hydrothermal treatment is done without using a catalyst. In other embodiments, the composition has not been subjected to one or more of hydrotreating, decarboxylation, decarbonylation, hydrodeoxygenation, isomerization (including hydroisomerization), desulfurization, denitrogenation, hydrocracking, and catalytic cracking. In one embodiment, the temperature is about 300 degrees Celsius and the hold time is about 30 minutes. In other embodiments, the temperature is about 260, about 265, about 270, about 275, about 280, about 285, about 290, about 295, or about 300 degrees Celsius. In yet other embodiments, the hold time is about 5, about 10, about 15, about 20, about 25, about 30, about 35, about 40, about 45, about 50, about 55, about 60, about 70, about 80, about 90, about 100, about 110, about 120, about 130, about 140, about 150, about 160, about 170, about 180, about 190, about 200, about 210, about 220, about 230, or about 240 minutes. In one embodiment, the extraction of the biomass comprises using a solvent. In other embodiments, the solvent is one or more hexane, heptane, cyclohexane, toluene (methylbenzene), chloroform (trichloromethane), methyl isobutyl ketone (MIBK), acetonitrile, ethanol, methyl-t-butyl ether (MTBE), methyl ethyl ketone (MEK), propanol, isopropyl alcohol (IPA), methanol, or methylene chloride (dichloromethane). In yet other embodiments, the solvent is a polar solvent, a non-polar solvent, or a combination of a polar and a non-polar solvent. In one embodiment, the solvent is one or more heptanes. In another embodiment, the solvent is methyl isobutyl ketone (MIBK).

Also provided herein are oleaginous compositions comprising an algal oil extracted from biomass comprising a non-vascular photosynthetic organism, made by a method comprising: a) obtaining the biomass; b) hydrothermally treating the biomass at a temperature from about 260 degrees Celsius to about 300 degrees Celsius, and holding the temperature from zero to about 240 minutes; c) acidifying the biomass; and d) extracting the composition from the biomass, wherein the algal oil comprises: from about 77.6 to about 78.0 weight percent Carbon; about 10.2 to about 10.6 weight percent Hydrogen; and about 3.0 to about 5.3 weight percent Nitrogen. In some embodiments, the algal oil further comprises from about 1.2 to about 1.4 weight percent Sulfur. In other embodiments, the algal oil further comprises from about 5.1 to about 7.2 weight percent Oxygen by difference. In yet other embodiments, the algal oil has a Hydrogen to Carbon ratio is about 1.63, is above 1.6, or is from about 1.6 to about 2.1. In one embodiment, the non-vascular photosynthetic organism is a microalga. In other embodiments, the microalga is a *Dunaliella* species, a *Scenedesmus* species, or a *Spirulina* species. In one embodiment, the hydrothermal treatment is done without using a catalyst. In other embodiments, the composition has not been subjected to one or more of hydrotreating, decarboxylation, decarbonylation, hydrodeoxygenation, isomerization (including hydroisomerization), desulfurization, denitrogenation, hydrocracking, and catalytic cracking. In some embodiments, the temperature is about 300 degrees Celsius and the hold time is about 30 minutes. In yet other embodiments, the temperature is about 260, about 265, about 270, about 275, about 280, about 285, about 290, about 295, or about 300 degrees Celsius. In some embodiments, the hold time is about 5, about 10, about 15, about 20, about 25, about 30, about 35, about 40, about 45, about 50, about 55, about 60, about 70, about 80, about 90, about 100, about 110, about 120, about 130, about 140, about 150, about 160, about 170, about 180, about 190, about 200, about 210, about 220, about 230, or about 240 minutes. In one embodiment, the biomass comprises using a solvent. In other embodiments, the solvent is one or more hexane, heptane, cyclohexane, toluene (methylbenzene), chloroform (trichloromethane), methyl isobutyl ketone (MIBK), acetonitrile, ethanol, methyl-t-butyl ether (MTBE), methyl ethyl ketone (MEK), propanol, isopropyl alcohol (IPA), methanol, or methylene chloride (dichloromethane). In some embodiments, the solvent is a polar solvent, a non-polar solvent, or a combination of a polar and a non-polar solvent. In one embodiment, the solvent is one or more heptanes. In another embodiment, the solvent is methyl isobutyl ketone (MIBK).

BRIEF DESCRIPTION OF THE DRAWINGS

These and other features, aspects, and advantages of the present disclosure will become better understood with regard to the following description, claims and accompanying figures where:

DETAILED DESCRIPTION

Figure 1A:
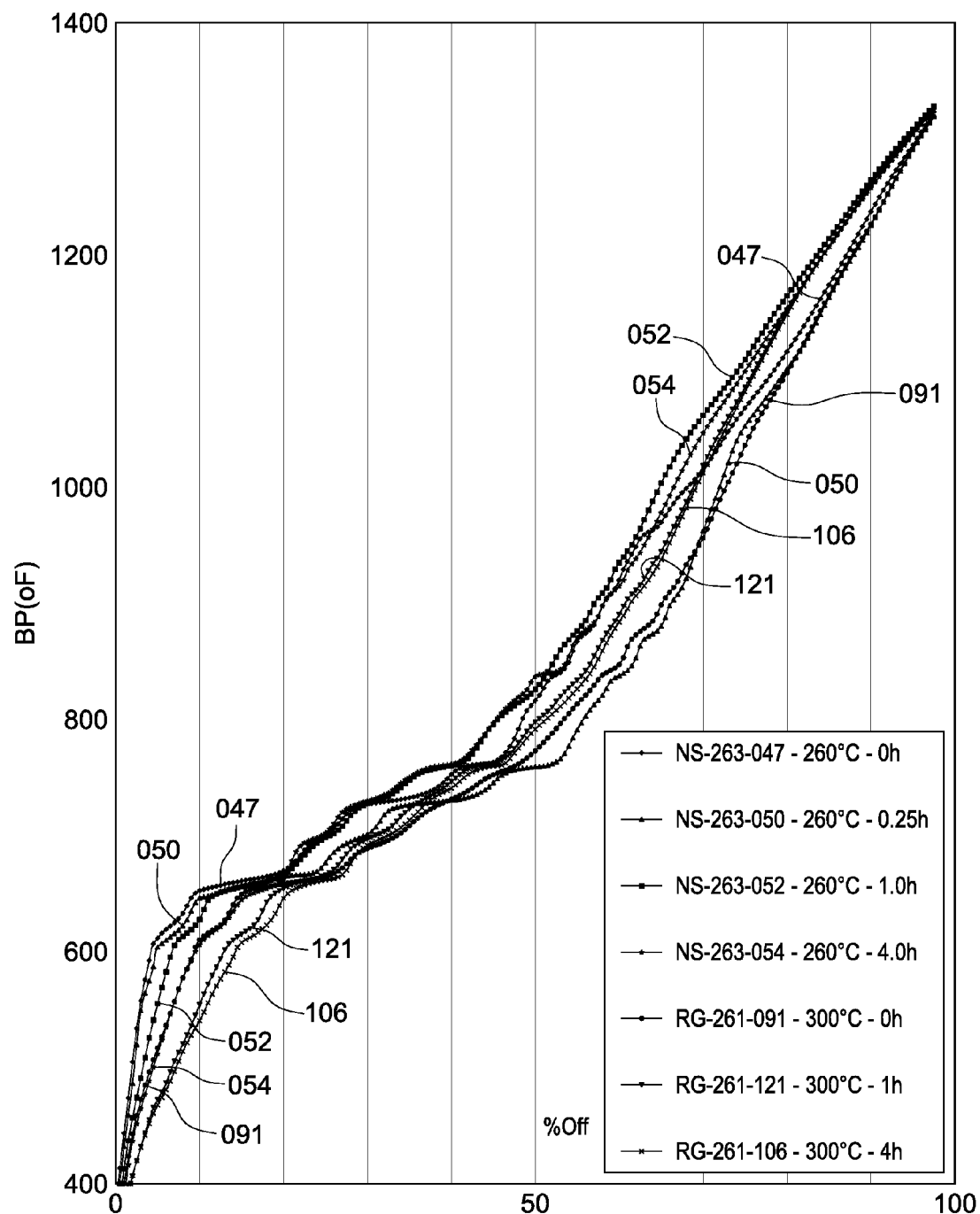
FIG. 1A is an overlay graph of boiling point curves (also called "distillation curves" or "boiling point distribution" showing BP in degrees F vs. % Off) for multiple algae oils described in EXAMPLE I according to some embodiments of the disclosure, wherein temperature and holding times of a hydrothermal treatment step in an extraction process were varied to include four holding times (0, 0.25, 1, and 4 hours) at 260 degrees C and three holding times (0, 1, and 4 hours) at 300 degrees C. The last three digits of each run/sample number (047, 050, 052, 054, 091, 121, and 106) are used to call-out the distillation curve of each sample.

The following detailed description is provided to aid those skilled in the art in practicing the present disclosure. Even so, this detailed description should not be construed to unduly limit the present disclosure as modifications and variations in the embodiments discussed herein can be made by those of ordinary skill in the art without departing from the spirit or scope of the present disclosure.

As used in this specification and the appended claims, the singular forms "a", "an" and "the" include plural reference unless the context clearly dictates otherwise.

Also, included as embodiments of the disclosure is a fraction or fractions of a crude algae oil, and methods of thermally treating the fraction or fractions. Also included as embodiments of the disclosure is wherein each of the values of yields, compound types, percent, area percent, weight percent, mass percent, fraction mass percent, simulated distillation fraction mass percent yields, simulated distillation fraction mass percent, compound type area percent, chemical compound type area percent, parts per million (ppm), weight percent, temperature, time, or pressure disclosed herein can have an "about" inserted before it, as one of average skill in the art will understand that "about" these values may be appropriate in certain embodiments of this disclosure.

In this disclosure, ranges of temperature and holding time/ residence time are given for many embodiments of the disclosure. It should be understood that the ranges are intended to include sub-ranges, and each incremental amount of temperature, time, and pressure, within each broad range given. For example, while a broad range of 200-600 degrees C temperature can be used in the embodiments of the disclosure, certain embodiments may include any of the following sub-ranges or any temperature within any of the following sub-ranges: 200-210, 210-220, 220-230, 230-240, 240-250, 250-260, 260-270, 270-280, 280-290, 290-300, 300-310, 310-320, 320-330, 330-340, 340-350, 350-360, 360-370, 370-380, 380-390, 390-400, 400-410, 410-420, 420-430, 430-440, 440-450, 450-460, 460-470, 470-480, 480-490, 490-500, 500-510, 510-520, 520-530, 530-540, 540-550, 550-560, 560-570, 570-580, 580-590, and/or 590-600 degrees C. For example, while the broad range of 0-24 hours holding time can be used in the embodiments of the disclosure, certain embodiments may include any of the following sub-ranges or any holding time within any of the following sub-ranges: 0 to 0.05, 0.05-0.1, 0.1-0.5, 0.5-1.0, 1.0-1.5, 1.5-2.0, 2.0-2.5, 2.5-3.0, 3.0-3.5, 3.5-4.0, 4.0-4.5, 4.5-5.0, 5.0-10.0, 10.0-15.0, 15.0-20.0, and/or 20.0-24.0 hours. Also, it should be understood that no holding time at a temperature may be effective (a zero holding time), especially when the temperature ramping schedule takes significant time.

As used in this specification and Claims, any range of values described as between two endpoints comprises the endpoints. For example, the range between 200 degrees C and 600 degrees C includes 200 degrees and 600 degrees C as well as all values in between.

As used in this specification and appended claims, the terms "hydrothermal treatment" and "hydrothermal process" are used interchangeably.

As used in this specification and appended claims, the term "biomass" refers to a composition of biological origin that is alive or has been alive within the last 50 years.

Abbreviations: HTT: hydrothermal treatment or processing; GC-MS: gas chromatography mass spectrometry; BP: boiling point; IBP: initial boiling point; HVGO; heavy vacuum gas oil; AEBP: atmospheric equivalent boiling point; MIBK: methyl isobutyl ketone; EA: elemental analysis; TDS: total dissolved solids; RBD: refining, bleaching, deodorizing; SIMDIST: simulated distillation; ASTM: American Society for Testing and Materials. This list is not a complete list of all abbreviations found throughout the disclosure.

Provided herein are methods and processes for obtaining an oleaginous compound or compounds from biomass and in particular a biomass comprising a microorganism. By an oleaginous compound is meant a compound having the properties of an oil. Thus, oleaginous compounds include hydrocarbons or lipids. Non-limiting examples of oleaginous compounds include, waxes; fatty acyls including free fatty acids, fatty esters and fatty amides; glycerolipids such as mono, di and tri glycerides; glycerophospholipids; sphingolipids such as phosphosphingolipids and glycosphingolipids; sterols; terpenes such as isoterpenes, isoprenes, terpenoids and isoprenoids; saccharolipids; polyketides; carotenoids, chlorophylls and other pigments. It is to be understood that any compound that can be extracted from biomass and refined into a fuel or lubricant may, in some embodiments, be considered an oleaginous compound.

Contrary to what is expected from the early proposals in patent and other literature for producing renewable fuels, crude algae oils have been produced by practical extraction techniques that comprise a wide range of molecular species that can be characterized by advanced analytical techniques. Further, as will be discussed in detail in other patent applications by the Applicants, the wide range of molecular species, while unusual compared to conventional refinery feedstocks, may be upgraded into fuels by conventional refining approaches such as hydrotreating and thermal treatment. In this sense, extracted algae oil can be understood as a unique bio-crude, but one which, with the help of advanced analytical techniques, may be fed to appropriate process units under conventional operating conditions and, in some cases, under adjusted operating conditions. The algae crude oils comprise a complex mixture of a large number of molecules having varying sizes and therefore varying boiling points. The crude algae oil is unique to its algae origins with corresponding unique compounds containing heteroatoms such as sulfur, nitrogen and oxygen, and also with unique types of molecules. The unique types of molecules fall generally into the paraffin, olefin and aromatic categories often used to characterize crude oils and oils from other sources, but are significantly different from petroleum crude and vegetable oils in terms of the specific compounds and amounts of compound classes. The properties of the complex mixtures that make up algae oils can be understood by various analytical techniques ranging from bulk measures, such as elemental analysis, to methods for understanding the molecular constituents in detail by methods such as GC-MS or HT GC-MS. These analyses allow these complex mixtures to be understood in a fuels context, to categorize the algae oil as potential feedstocks for conventional petroleum fuel refineries and to predict how they will upgrade in the conventional refineries. In this sense, the algae oil compositions are unexpected and their properties are unique.

Further, because of the unique compositions of the algae oils, the products from upgrading of these algae oils in conventional refinery units are expected to be unique, as will be further disclosed and claimed in other patent applications. For example, oils derived from petroleum, with a boiling point distribution of kerosene/distillate, gas oil and residuum, would be expected to yield roughly the same amount of products when they are hydrotreated but with a lower heteroatom content. Extracted crude algae oils have been shown by the Applicants to behave differently from this, for example, in that they upgrade with substantial conversion from one boiling point fraction to another when they are thermally processed and/or hydrotreated. This different behavior in thermal processing and/or hydrotreatment will be important in achieving a flexible and high quality product slate from algae oils, whether or not they are blended with conventional fossil petroleum and/or vegetables oils. As will also be disclosed in other patent applications, this substantial conversion to lower point fractions, under low- to moderate-severity conditions, when combined with recycling of unconverted fraction(s), will allow a refiner to obtain up to 80-100% of a fraction selected from the list of naphtha's (butanes to 430 F), distillates (430-650 F), and gas oils (650-1000 F), for example.

The compositions of matter may be extracted from lipid-containing microorganisms, which may include microorganisms capable of photosynthesis, such as photosynthetic microalgae, photosynthetic macroalgae, cyanobacteria, and photosynthetic bacteria. These microorganisms are especially useful due to their ability to remove carbon dioxide from the atmosphere and the fact that they do not directly compete with food production for resources.

In certain embodiments of this disclosure, the biomass is substantially algae, for example, over 80 wt % algae, or over 90 wt % algae. In the Examples of this disclosure, the biomass is photosynthetic algae grown in light. Other embodiments, however, may comprise obtaining algae biomass or other "host organisms" that are grown in the absence of light. For example, in some instances, the host organisms may be photosynthetic organisms grown in the dark or organisms that are genetically modified in such a way that the organisms' photosynthetic capability is diminished or destroyed. In such growth conditions, where a host organism is not capable of photosynthesis (e.g., because of the absence of light and/or genetic modification), typically, the organism will be provided with the necessary nutrients to support growth in the absence of photosynthesis. For example, a culture medium in which an organism is grown, may be supplemented with any required nutrient, including an organic carbon source, nitrogen source, phosphorous source, vitamins, metals, lipids, nucleic acids, micronutrients, and/or an organism-specific requirement. Organic carbon sources include any source of carbon which the host organism is able to metabolize including, but not limited to, acetate, simple carbohydrates (e.g., glucose, sucrose, and lactose), complex carbohydrates (e.g., starch and glycogen), proteins, and lipids. One of skill in the art will recognize that not all organisms will be able to sufficiently metabolize a particular nutrient and that nutrient mixtures may need to be modified from one organism to another in order to provide the appropriate nutrient mix.

Of particular interest are algal microorganisms, and algae-derived oils (herein "algal oil" and also "crude algal oil") that have been extracted from algal biomass and that have unusual compositions as compared to conventional fossil crude oils and vegetables oils. The extracted algae oils comprise an unexpectedly-wide range of compounds, including compounds significantly different from those in fossil and vegetable crude oils, that is, different either in identity and/or amount. For example, algae oil in embodiments of the disclosure include large amounts of amides, nitrogen-containing compounds, fatty acids, unsaturated hydrocarbons, nitriles, oxygen-containing compounds, phosphorous compounds, and sterols, compared to conventional fossil crude oils and vegetables oils. The resulting algae oil characteristics, for example, high acid and nitrogen and oxygen content, may cause concern for fossil petroleum refiners, who avoid feedstock changes that might cause operating upsets, shortened catalyst life, and/or corrosion of equipment. However, processing of certain of the novel algae oils, by thermal treatment, hydrotreatment, and/or deoxygenation methods, has shown that moderate unit conditions, moderate hydrogen usage, and conventional catalysts, may be used to successfully upgrade the algae oils with advantageous results. Such processing, as described in other patent applications by the Applicants, has achieved heteroatom removal, boiling point/density improvement, and/or desirable cracking resulting in a product slate, and flexibility to adjust the product slate, that is desirable for conventional refineries.

The crude oils of embodiments of the disclosure may be one or more crude oils extracted by various means from naturally-occurring non-vascular photosynthetic organisms and/or from genetically modified non-vascular photosynthetic organisms. Genetically modified non-vascular photosynthetic organisms, can be used, for example, wherein the chloroplast or nuclear genome of an algae is transformed with a gene of interest. As used herein, the term non-vascular photosynthetic organism includes, but is not limited to, macroalgae, microalgae and cyanobacteria (blue-green algae). Therefore, crude algae oil may be obtained from naturally-occurring algae (non-genetically-modified) and genetically-modified algae. Crude algae oil may be obtained from the natural or modified algae wherein growing conditions, for example, nutrient levels, light, or the salinity of the media in which the algae are grown, are controlled or altered to obtain a desired phenotype, or to obtain a certain lipid composition or lipid panel.

As discussed above, algae may be macroalgae and/or microalgae and the term microalgae includes, for example, microalgae (such as *Nannochloropsis* sp.), cyanobacteria (blue-green algae), diatoms, and dinoflaggellates. Therefore the biomass in which the crude algae oil is obtained from can comprise a mixture of one or more of an algae, such as a microalgae and one or more of a cyanobacteria.

Several, but not the only, examples of algae from which a suitable crude oil may be obtained are a *Chlamydomonas* sp., a *Dunaliella* sp., a *Scenedesmus* sp., a *Desmodesmus* sp., a *Chlorella* sp., a *Volvacales* sp., a *Volvox* sp., an *Arthrospira* sp., a *Sprirulina* sp., a *Botryococcus* sp., a *Desmid* sp., a *Hematococcus* sp., a *Nannochloropsis* sp, or any combination of one or more species of the above species.

Non-limiting examples of organisms from which suitable a crude oil may be obtained include *Chlamydomonas reinhardtii, Dunaliella salina, Haematococcus pluvialis, Nan-* nochloropsis oceania, Nannochloropsis salina. Scenedesmus dimorphus, Spirulina maximus, Arthrospira fusiformis, Dunaliella viridis, Nannochloropsis oculata, or Dunaliella tertiolecta, or any combination of one or more species of the above organisms.

Examples of cyanobacteria from which a suitable crude oil may be obtained include Synechococcus sp., Spirulina sp., Synechocystis sp., Athrospira sp., Prochlorococcus sp., Chroococcus sp., Gleoecapsa sp., Aphanocapsa sp., Aphanothece sp., Merismopedia sp., Microcystis sp., Coelosphaerium sp., Prochlorothrix sp., Oscillatoria sp., Trichodesmium sp., Microcoleus sp., Chroococcidiopisis sp., Anabaena sp., Aphanizomenon sp., Cylindrospermopsis sp., Cylindrospermum sp., Tolypothrix sp., Leptolyngbya sp., Lyngbya sp., or Scytonema sp., or any combination of one or more species of the above species.

The non-vascular photosynthetic organisms can be grown on land, for example, in ponds, race-way ponds, aqueducts, landfills, or in closed or partially closed bioreactor systems. The organisms can also be grown directly in water, for example, in an ocean, sea, lake, river, reservoir, etc. In embodiments where the organism is mass-cultured, the organism may, but need not be, grown in high density bioreactors using methods known in the art. For example, algae can be grown in high density photobioreactors (see, e.g., Lee et al, Biotech. Bioengineering 44:1161-1167, 1994) and other bioreactors (such as those for sewage and waste water treatments) (e.g., Sawayama et al, Appl. Micro. Biotech., 41:729-731, 1994). In some embodiments, algae may not be mass-cultured primarily for its oil content but, for example, to remove heavy metals (e.g., Wilkinson. Biotech. Letters, 11:861-864, 1989), produce hydrogen (e.g., U.S. Patent Application Publication No. 20030162273), or to produce nutritional supplements or therapeutic compounds (Walker et al., Plant Cell Rep. 24:629-641, 2005).

The aqueous environment containing the non-vascular photosynthetic organisms can be water from any natural source without treatment and/or without supplementation. The water can be fresh water, brackish water, or sea water. In some embodiments the aqueous environment may contain 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3 molar or higher concentrations of sodium chloride. One of skill in the art will recognize that other salts (sodium salts, calcium salts, potassium salts, etc.) may also be present in the aqueous environment. A method of measuring water quality is total dissolved solids (TDS). TDS is well known in the area of water quality and is a measure of the combined content of organic and inorganic substances dissolved in the water. In general, fresh water has a TDS of less than 1500 mg/l, brackish water has a TDS of from 1500 to 5000 mg/l and saline water has a TDS of greater than 5000 mg/l. Thus, in some embodiments, the aqueous environment can have TDS of up to 1500 mg/l, 2,000 mg/l, 2500 mg/l, 3000 mg/l, 3500 mg/l, 4000 mg/l, 4500 mg/i, 5000 mg/l, 5500 mg/l, 6000 mg/l, 6500 mg/l, 7000 mg/l, 7500 mg/l, 8000 mg/l, 8500 mg/l, 9000 mg/l, 10000 mg/l, 10500 mg/l, 11000 mg/l, 11500 mg/l, 12000 mg/l, 12500 mg/l, 13000 mg/l, 13500 mg/l, 14000 mg/l, 14500 mg/l, or 15000 mg/l.

Another way to classify water is by salinity. Salinity is a measure of the total dissolved salts in water and is traditionally measured in parts per thousand (‰). In certain embodiments the aqueous environment has a salinity of less than 0.5‰, from 0.5 to 3‰, from 4 to 29‰ from 30 to 50‰ or greater than 50‰. In other embodiments, the aqueous environment may be water that is not from a natural source. That is, the water composition and/or chemistry may be modified to provide the desired environment for the growth of the non-vascular photosynthetic organism. For example and without limitation, in one embodiment the salt concentration of the water may be increased or decreased. In another embodiment, the pH of the water may be raised or lowered. In still another embodiment, the concentration of $CO_2$ in the water may be increased.

In some embodiments, the aqueous environment containing the non-vascular photosynthetic organism may be supplemented with nutrients. The supplemental material may be elemental in nature, for example, nitrogen, potassium, phosphorous, etc. delivered either in elemental form or in other forms such a nitrates, potassium salts, etc. In other embodiments, the aqueous environment is supplemented with energy sources such as simple sugars, complex carbohydrates, etc. Various water-based media are known in the art for growing non-vascular photosynthetic organisms such as microalgae and cyanobacteria and can be utilized.

In still other embodiments, the aqueous environment is supplemented with compounds to protect the non-vascular photosynthetic organism of interest from predator organisms or contaminating organisms. Such compounds include herbicides, pesticides, bactericides and bacteriostats, used alone or in combination. The non-vascular photosynthetic organism which is being cultivated can be naturally resistant to the compounds, can be resistant to the compound due to introduction of a mutation, can be genetically engineered to be resistant to the compound, or can be artificially selected for increased resistance to the compounds.

In some embodiments, the water content of the biomass is reduced prior to conducting an extraction process. Non-limiting examples of methods for reducing the water content (dewatering) of feedstock comprising aquatic biomass, and in particular non-vascular photosynthetic organisms include, flocculation, centrifugation and filtration. It will be apparent to one of skill in the art that one or more of these methods may be combined to accomplish dewatering. For example, flocculation may be combined with centrifugation and/or filtration.

One method of increasing the concentration of non-vascular photosynthetic organisms is to flocculate or aggregate the organisms to facilitate removal from the aqueous environment. Flocculants or flocculating agents promote flocculation by causing colloids and other suspended particles (e.g., cells) in liquids to aggregate, forming a flocculant. Flocculants are used in water treatment processes to improve the sedimentation of small particles. For example, a flocculant may be used in swimming pools or drinking water filtration to aid removal of microscopic particles which would otherwise cause the water to be cloudy and which would be difficult to remove by filtration alone.

Many flocculants are multivalent cations such as aluminum, iron, calcium or magnesium. These positively charged molecules interact with negatively charged particles and molecules to reduce the barriers to aggregation. In addition, many of these chemicals, under appropriate pH and other conditions such as temperature and salinity, react with water to form insoluble hydroxides which, upon precipitating, link together to form long chains or meshes, physically trapping small particles into the larger flocculant.

Flocculation of non-vascular photosynthetic organisms such as microalgae and cyanobacteria using chemical flocculants is well known in the water treatment arts. Long-chain polymer flocculants, such as modified polyacrylamides, are commercially available. These are supplied in dry or liquid form for use in the flocculation process. One of the most common flocculants, liquid polyacrylamide, is typically supplied as an emulsion with 10-40% actives and the rest is a carrier fluid, surfactants and latex.

An alternative to chemical flocculation is biological flocculation. In biological flocculation, the non-vascular photosynthetic organism may be genetically engineered to produce one or more flocculation moieties on its surface. The flocculation moieties can be expressed constitutively or expression can be induced, for example, by the use of an inducible promoter. The flocculation moiety can be, for example, a carbohydrate or protein binding moiety that binds to a surface protein or carbohydrate located on the external surface of the non-vascular photosynthetic organism. In such a case, expression of the flocculation moiety causes the non-vascular photosynthetic organisms to bind to each other to form a flocculant. In other non-limiting examples the population of non-vascular photosynthetic organisms contains sub-populations of microorganisms that have been genetically engineered to express complementary flocculation moieties on their surfaces, for example a carbohydrate binding lectin and its corresponding carbohydrate or an antibody and its corresponding antigen. Flocculation can be induced by growing the two populations separately and then mixing them, or alternatively, inducing expression of one or both of the molecules involved in flocculation. In another example, an organism that is genetically modified to produce and secrete a flocculation moiety can be used. Further examples of biological flocculation can be found in International Patent Application Publication WO 2009/158658.

In another embodiment, dewatering can be achieved by filtration, for example by membrane filtration. In this method, water permeates through the membranes and the non-vascular photosynthetic organisms become more concentrated on one side of the membranes. Typically, the membranes operate under a slight vacuum induced by a permeate pump, which pumps away water that flows through the membrane. Compressed air may be fed to the bottom of the membrane module to prevent solids from accumulating on the outside surface of the membranes. The air also provides agitation that keeps the non-vascular photosynthetic organisms suspended. Permeate water is also periodically pumped in reverse (from the inside to the outside of the membrane) to remove any particles that may be lodged in the membrane interstices.

Additionally, dewatering may be accomplished by centrifugation. As is known in the art, a centrifuge uses rotation around a fixed axis to generate centripetal acceleration resulting in the separation of materials based on density. Separation using centrifugation can be accomplished in a batch or continuous process. Typically, a continuous process is used for large volumes. In one embodiment a disc stack centrifuge is used. In another embodiment, a decanter centrifuge is used. Disc stack and decanter centrifuges are well known in the art and commercially available from a number of manufacturers. Centrifugation may be applied to untreated material or used in combination with additional dewatering processes such as flocculation and/or filtration. By way of example and not limitation, material may be first subjected to flocculation followed by centrifugation of the flocculant resulting in biomass having a water content of about 75%, about 80%, about 85%, about 90%, about 95% or about 99%.

Several techniques are known for extracting oil from biomass. Conventional techniques include harvesting and drying algae and then extracting the oil from the lysed or destroyed cells. The cells may be chemically lysed, or mechanical force can be used to destroy cell walls. Oil may be extracted from the lysed/destroyed cells using an organic solvent such as hexane.

The Applicants believe that algae oil extraction methods comprising hydrolysis may be important in achieving the unusual algae oils of certain embodiments of the disclosure. In certain embodiments of the present disclosure, the algae oil compositions are obtained by a novel hydrothermal extraction technique, which comprises hydrolysis of lipids and/or other compounds in the biomass. Such extraction methods may comprise heating, cooling, and acidifying the biomass, followed by re-heating and solvent addition, separation of an organic phase and an aqueous phase, and removal of solvent from the organic phase to obtain an oleaginous composition. Various solvents may be used, for example, heptanes, hexanes, and/or MIBK.

Hydrothermal treatment/extraction methods are believed to hydrolyze lipids and other compounds of the algae biomass, and to result in extracted algae oil that is high in fatty acids. Not all compounds contained in algae or hydrothermally-treated algae oil can currently be identified, and the pathways of hydrolysis and other reactions that lead to the compounds present in hydrothermally-extracted algae oil are numerous and complex. This is due in part to other portions of the algae (proteins, carbohydrates, nucleic acids, cell walls, for example) reacting and producing intermediate products that may react with each other to produce new molecules. The complexity of algae and the numerous reactions that are possible during hydrothermal treatment may be illustrated by referring to a list of lipids that the Applicants believe to be present in various algae strains, for example (but not limited to): Triacylglycerols, Diacylglycerols, Monoacylglycerols, Sterols, Sterol Esters, Wax Esters, Tocopherols. Fatty Acids, Phosphatidic Acid (PA), Lysophosphatidic Acid. Phosphatidyl glycerol (PG), Cardiolipin, Phosphatidyl choline (PC), Lysophospatidyl choline, Phosphatidyl ethanolamine (PE), Phosphatidyl serine (PS), Phosphatidylinositol (PI), Phosphonyl ethanolamine, Ether Lipids, Monogalactosyl diacylglycerol (MGDG), Digalactosyl diacylglycerol (DGDG), Sulfoquinovosyl diacylglycerol (SQDG), Sphingosine, Phytosphingosine, Sphingomyelin, Glucosylceramide, Diacylglyceryl trimethylhomoserine (DGTS), Ricinoleic Acid, Prostaglandin, Jasmonic Acid, α-Carotene, β-Carotene, β-Cryptoxanthin, Astaxanthin, Zeaxanthin, Chlorophyll a, Chlorophyll b, Pheophytin a, Phylloquinone, and Plastoquinone. Many of these compounds are converted to hydrolysis products, to a greater or lesser extent depending on the temperature and reaction time of the hydrothermal treatment, and thus will be reduced or eliminated from the hydrothermally-treated extracted algae oil. Of these many lipids, triglycerides may be of interest because they make up nearly 100 percent of many vegetables oils that have been proposed for renewable fuels; it may be noted that the hydrolysis step discussed herein may lower the triglyceride content in many crude algae oil embodiments of the disclosure to less than about 1 area % or more typically less than about 0.05 area %, as measured by HT GC-MS. The high fatty acid content of many crude algae oil embodiments of the disclosure, for example, are about 15 area % up to about 60 area % or more, and may be attributed at least in part to hydrolysis of lipids.

The hydrothermal extraction methods used for the crude algae oil embodiments detailed in the Tables and Figures of this document were extracted from algae biomass by the processes described in U.S. Patent Application No. 61/432,006, filed Jan. 12, 2011, and U.S. Ser. No. 13/191,373, filed Jul. 26, 2011, now U.S. Pat. No. 8,192,628, comprising heating, cooling, acidifying, re-heating, adding solvent with re-heating, separating an organic phase and an aqueous phase, and removing solvent from the organic phase to obtain an oleaginous composition. The entire disclosure of this provisional application is incorporated herein by this reference. It should be noted that the extraction methods may be conducted as a batch, continuous, or combined process. Specifically, unless otherwise specified herein, the extraction process was:

a) obtaining an aqueous composition comprising the biomass and water;
b) heating the aqueous composition in a closed reaction vessel to a first temperature between about 250 degrees C and about 360 degrees C and holding at the first temperature for a time between 0 and 60 minutes;
c) cooling the aqueous composition of (b) to a temperature between ambient temperature and about 150 degrees C;
d) acidifying the cooled aqueous composition of (c) to a pH from about 3.0 to less than 6.0 to produce an acidified composition;
e) heating the acidified composition of (d) to a second temperature of between about 50 degrees C and about 150 degrees C and holding the acidified composition at the second temperature for between about 0 and about 30 minutes;
f) adding to the acidified composition of (e) a volume of a solvent approximately equal in volume to the water in the acidified composition to produce a solvent extraction composition, wherein the solvent is sparingly soluble in water, but oleaginous compounds are at least substantially soluble in the solvent;
g) heating the solvent extraction composition in closed reaction vessel to a third temperature of between about 60 degrees C and about 150 degrees C and holding at the third temperature for a period of between about 15 minutes and about 45 minutes;
h) separating the solvent extraction composition into at least an organic phase and an aqueous phase;
i) removing the organic phase from the aqueous phase; and
j) removing the solvent from the organic phase to obtain an oleaginous composition.

The details of hydrothermal extraction, such as temperature, holding time, and solvent, may affect the composition of the crude algae oil. However, the Applicants have analyzed crude algae oil obtained from several different hydrothermal extraction methods within the scope of the above-listed steps, with several solvents. These several different hydrothermal extraction methods have yielded extracted algae oils that have slight differences in composition, and boiling point and molecular weight distributions, but that are within the broad scope of the disclosure as it is discussed in this Description and in the Claims. Therefore, embodiments of the disclosure are not necessarily limited to algae oils extracted under the specific hydrothermal conditions disclosed herein, and other extraction methods, including methods other than hydrothermal methods, may be found that produce the unusual compositions of the crude algae oil.

Different algae strains and/or different growing conditions may also affect the composition of the crude algae oil. However, the Applicants have analyzed crude algae oil extracted hydrothermally from several different algae strains, with only moderate differences in composition. For example, heteroatom content and sterol content differences have been noted.

The strain-related and extraction-related differences have been minor compared to the greater differences between hydrothermally-extracted algae oils and conventional oils such as fossil crude oils and vegetable oils. The slightly or moderately different fingerprints and compositions of crude algae oil from different strains and extraction techniques are still within the broad scope of the disclosure as disclosed in the Claims.

The crude algae oil compositions are typically not processed or treated between the above-described extraction process and any molecular and/or chemical analysis to determine the crude algae oil composition. For example, the crude algae oil is not hydrotreated, hydrocracked, reformed, filtered, chemically-treated, or fractionated after being extracted and before analysis. The crude algae oil need not be subjected to any RBD processing (the refining, bleaching, and deodorizing process conventionally known and used for many bio-oils), and need not be subjected to any of the individual steps of refining, bleaching or deodorizing, after being extracted and before analysis.

In one embodiment, the feedstock comprising biomass is subject to a pretreatment after step a) above. The feedstock may be any biomass such as those described herein, and in particular a non-vascular photosynthetic organism. In one embodiment, the biomass comprises one or more alga or cyanobacterium. The feedstock used in the pretreatment may contain about 50%, about 60%, about 70%, about 80%, about 85%, about 90%, about 95% or about 99% water. During the pretreatment, the biomass is heated to a pretreatment temperature between about 80 degrees C and about 220 degrees C. In certain embodiments the pretreatment temperature is between about 100 degrees C and 210 degrees C, between about 160 degrees C and 200 degrees C or between about 170 degrees C and 210 degrees C. In some embodiments the pretreatment temperature is between about 180 degrees C and 200 degrees C. The material may be held at the pretreatment temperature from between about 5 minutes and 60 minutes. In certain embodiments, the feedstock is held at the pretreatment temperature for between about 20 minutes to 40 minutes. As will be appreciated by those skilled in the art, equivalent pretreatments may be obtained with various combinations of time and temperature. For example, as temperature is increased, the amount of time required may decrease. In particular embodiments, pretreatment of the biomass comprises heating to between about 170 degrees C and 210 degrees C for between about 20 minutes to 40 minutes; to between about 160 degrees C and about 180 degrees C for between about 30 minutes and 60 minutes; and between about 180 degrees C and 200 degrees C for between about 25 minutes and 35 minutes.

In some embodiments, the feedstock (biomass) is subjected to mixing during the pretreatment, while in other embodiments no mixing is used. When mixing is utilized, it can be intermittent or constant. The mixing can be accomplished by any method known in the art. In one embodiment, mixing is accomplished using an impeller, rotor or paddle. In another embodiment, mixing is achieved by use of a pump. Other methods of mixing the feedstock will be readily apparent to those of skill in the art.

In some embodiments, acid is added to the feedstock during pretreatment. If used, the acid may be added prior to or during heating the material to the pretreatment temperature. Addition of the acid, may result in the feedstock having a pH of between about 3 and 6. In certain embodiments the biomass will be acidified to a pH of about 3, about 4, about 5 or about 6 during the pretreatment process. Any acid may be used in the pretreatment process. In some embodiments, a strong acid such as HI, $H_2SO_4$, HBr, HCl, $H_1PO_4$, $HNO_3$ or $CH_3SO_3H$ is used.

In some embodiments, liquid may be removed from the pretreated material. Removal of liquid may be achieved by any method known in the art, such as those described herein. For example following pretreatment, the material may be allowed to phase separate into at least a solids and liquid phase, and the phases separated by, for example decanting, siphoning, draining or pumping. In other embodiments, the liquid phase may be removed by filtration or centrifugation such as described herein. Exemplary methods of centrifugation include the use of stacked disc and decanter centrifuges.

In some embodiments, the pretreatment may further comprise rinsing the biomass. If rinsing is utilized, the rinse liquid, for example water, is added to the biomass following heating and removal of the liquid phase. The amount of rinse liquid used in rinsing may vary between 25% and 200% of the volume of the liquid phase removed following heating. In certain embodiments, rinsing involves mixing of the biomass and the added rinse liquid for between about 5 minutes and 60 minutes. In particular embodiments, the biomass and rinse liquid are mixed for between about 5 minutes and about 10 minutes, between about 10 minutes and about 20 minutes, between about 20 minutes and about 30 minutes, between about 25 minutes and about 30 minutes, between about 30 minutes and 40 minutes, between about 40 minutes and about 50 minutes, or between about 50 minutes and about 60 minutes. After mixing, the added rinse liquid may be removed using any of the methods described herein including gravity separation, centrifugation and filtration.

Following pretreatment, the pretreated feedstock may be processed further to obtain oleaginous compounds or it may be stored. If the material is stored, it may be stored for any time period ranging from 1 day to 1 year. For example, the pretreated feedstock may be stored for a period from 1 day to 1 month, from 1 month to 3 months, from 3 months to 6 months, from 6 months to 9 months or from 9 months to 12 months. The pretreated feedstock may be stored at ambient temperature or it may be stored at a controlled temperature. If the material is stored at a controlled temperature, the storage temperature may be between 0 degrees C and ambient temperature. In certain embodiments, the storage temperature can be between about −20 degrees C and about −10 degrees C, between about −10 degrees C and about −5 degrees C, between about −5 degrees C and about 0 degrees C, between about 0 degrees C and about 5 degrees C, between about 5 degrees C and about 10 degrees C, between about 10 degrees C and about 15 degrees C, between about 10 degrees C and about 20 degrees C, between about 15 degrees C and about 20 degrees C, or between about 20 degrees C and about 25 degrees C.

The pretreated feedstock may be stored in an open container, a container that is covered but open to the atmosphere, or a closed container (i.e. not open to the atmosphere). If a closed container is utilized, there may be a headspace, that is, the space between the top of the stored material and the top of the container. If such a headspace is present, the atmosphere in the headspace can be air or some artificial atmosphere. For example, the atmosphere in the headspace may contain an inert gas such as nitrogen, carbon dioxide or argon. In certain embodiments the atmosphere in the headspace may be maintained at a pressure greater or lesser than normal atmospheric pressure.

In one embodiment the feedstock comprising biomass and water is subject to hydrothermal treatment or processing (HTT) and in particular hydrothermal liquefaction, with or without prior pretreatment. In one embodiment, the feedstock is an aqueous slurry containing biomass. In another embodiment, the feedstock is an aqueous medium containing a non-vascular photosynthetic organism, for example a microalga or a bacterium. In certain embodiments, the non-vascular photosynthetic organism is an alga or a cyanobacterium (blue green alga). The feedstock will typically, but not necessarily, contain about 50%, about 60%, about 70%, about 80%, about 85%, about 90%, about 95% or about 99% water. In certain, embodiments, a liquid, for example water, may be added to the feedstock to increase the moisture content. For example, if dried, pretreated and/or stored feedstock is used, liquid may be added.

The feedstock is introduced into a closed reaction vessel. The feedstock can be introduced by any suitable method, but is typically introduced using a pipe. The feedstock can be moved into the reaction chamber using known techniques. In one embodiment the feedstock is moved by the use of pumps, while in other embodiments gravity flow is used.

In the hydrothermal treatment, the initial feedstock can be heated to a hydrothermal processing temperature of between about 180 degrees C and about 600 degrees C or between about 250 degrees C and about 500 degrees C. In certain embodiments the hydrothermal processing temperature is between about 250 degrees C and about 370 degrees C. In other embodiments the initial feedstock is heated to a temperature between about 250 degrees C and about 270 degrees C. In still other embodiments, the initial feedstock is heated to a temperature between about 270 degrees C and about 330 degrees C, between about 280 degrees C and about 320 degrees C, or between about 290 degrees C and about 310 degrees C. In additional embodiments, the initial feedstock is heated to a temperature of about 250 degrees C, about 260 degrees C, about 270 degrees C, about 280 degrees C, about 290 degrees C, about 300 degrees C, about 310 degrees C, about 320 degrees C, about 330 degrees C, about 340 degrees C, about 350 degrees C, about 360 degrees C, about 375 degrees C, about 400 degrees C, about 425 degrees C, about 450 degrees C, about 475 degrees C or about 500 degrees C. In one embodiment, the initial feedstock is rapidly heated to the final temperature, for example, over a period of about 5 minutes, about 10 minutes, about 15 minutes, about 20 minutes, about 30 minutes, about 40 minutes, about 50 minutes, or about 60 minutes. The initial feedstock may be held at the hydrothermal processing temperature for a period of between about 0 minutes (i.e. no hold time) and about 15 minutes, about 30 minutes, about 60 minutes, about 90 minutes, about 2 hours, about 3 hours or about 4 hours. In other embodiments, the feedstock is held at the hydrothermal processing temperature for from about 10 minutes to about 30 minutes, from about 30 minutes to about 90 minutes or from about 90 minutes to about 120 minutes. In certain embodiments, the initial feedstock is held at the hydrothermal processing temperature for 1 minute, about 5 minutes, about 10 minutes, about 15 minutes, about 20 minutes, about 25 minutes, about 30 minutes, about 35 minutes, about 40 minutes, about 45 minutes, about 50 minutes, about 55 minutes, about 60 minutes, about 90 minutes, about 120 minutes, about 150 minutes, about 180 minutes, about 210 minutes or about 240 minutes.

The hydrothermal processes can be carried out with or without the use of a catalyst. Catalysts that may be used include $Fe(CO)_5$—S, $Na_2CO_3$, and KOH, $Fe(CO)_5$—S may be used at a concentration of from 0 to 1 mmol. $Na_2CO_3$ and KOH can be used at a concentration of from 0 to 1.0 M.

In some embodiments, the feedstock is subjected to mixing during the hydrothermal processing, while in other embodiments no mixing is used. When mixing is utilized, it can be intermittent or constant. The mixing can be accomplished by any method known in the art. In one embodiment, mixing is accomplished using an impeller, rotor or paddle. In another embodiment, mixing is achieved by use of a pump. Other methods of mixing the feedstock will be readily apparent to those of skill in the art.

Also during the hydrothermal processing the pressure within the reaction vessel increases due to the heating of the contents of the vessel. The pressure during the process need not be held at a particular level, but is maintained at a pressure high enough to prevent vaporization (phase change or boiling) of the liquid in the vessel and below the pressure rating of the reaction vessel. During hydrothermal processing, excess gas may be vented from the reaction vessel. Venting may be continuous or intermittent. For example, gas may be vented about every 5 minutes, every 10 minutes, every 15 minutes, every 20 minutes, every 25 minutes or every 30 minutes. As is well known in the art, the point at which there is phase change from a liquid to a vapor (e.g. boiling point) is affected by both temperature and pressure. It is well within the ability of the skilled artisan to determine the minimum pressure that must be maintained to prevent a phase change at any given temperature.

The vented gas which often contains high levels of $CO_2$ can be vented to the atmosphere or the gas can be captured and used for other purposes. In one embodiment, the $CO_2$ produced is captured and utilized for growing additional biomass. In another embodiment, ammonia gas produced is captured and used as a source of nitrogen for growing additional biomass.

In some embodiments, the headspace in the hydrothermal processing reaction vessel contains an inert gas such as nitrogen, argon or carbon dioxide. In other embodiments the headspace contains air. In certain embodiments, the headspace initially contains air or an inert gas, but during the hydrothermal processing the initial gas in the headspace is displaced by gases emitted from the feedstock during the hydrothermal processing.

In some embodiments, the hydrothermal processing is carried out as a batch process. That is, an amount of feedstock is added to the hydrothermal processing reaction vessel, the hydrothermal process completed, and the contents of the reaction vessel removed. In other embodiments, a continuous process is used. In the continuous process, new feedstock is added and hydrothermal process product is removed on a continuing basis. The addition of feedstock and removal or product may be intermittent or it may be continuous.

The product of the hydrothermal treatment or processing is then cooled to a temperature between ambient temperature and about 150 degrees C. In certain embodiments, the hydrothermal processing product is cooled to a temperature between about 30 degrees C and about 150 degrees C, between about 30 degrees C and about 120 degrees C, between about 100 degrees C and about 150 degrees C, between about 110 degrees C and about 130 degrees C, between about 50 degrees C and about 70 degrees C or between about 55 degrees C and about 65 degrees C. In other embodiments, the product of the hydrothermal processing cooled to a temperature of about 30 degrees C, about 35 degrees C, about 40 degrees C, about 45 degrees C, about 50 degrees C, about 55 degrees C, about 60 degrees C, about 65 degrees C, about 70 degrees C, about 75 degrees C, about 80 degrees C, about 85 degrees C. about 90 degrees C, about 95 degrees C, about 100 degrees C, about 105 degrees C, about 110 degrees C, about 115 degrees C, about 120 degrees C, about 125 degrees C, about 130 degrees C, about 135 degrees C, about 140 degrees C, about 145 degrees C and about 150 degrees C.

Following cooling, the hydrothermal processing product is acidified to a pH between about 2.0 and about 6.0, between about 2.0 and about 3.0, between about 3.0 and about 4.0, between about 4.0 and about 5.0, between about 3.5 and about 4.5, between about 3.6 and about 4.4, between about 3.7 and about 4.5, between about 3.8 and about 4.6, between about 3.9 and about 4.7, between about 4.0 and about 4.8, between about 4.5 and about 5.0, between about 5.0 and about 5.5 or between about 5.5 and about 6.0. In other embodiments, the cooled product of the hydrothermal processing is acidified to a pH of about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, or about 6.0. In still other embodiments, the product of hydrothermal processing is acidified to a pH from about 2.0 to less than 6.0, from about 3.0 to less than 6.0 or from about 4.0 to less than 6.0. Any acid may be used in the acidification process. In some embodiments, a strong acid such as HI, $H_2SO_4$, HBr, HCl, $H_3PO_4$, $HNO_3$ or $CH_3SO_3H$ is used. The acidification process is typically, but not necessarily, carried out at atmospheric pressure, with mixing. Alternatively, the acidification process is carried out at the vapor pressure of the solution containing water, biomass, acid and solvent. Acidification following, rather than before or during hydrothermal processing has several advantages. Thus in one embodiment, the biomass is not acidified (i.e. there is no addition of acid) prior to or during hydrothermal processing. In another embodiment there is no addition of acid following pretreatment or during hydrothermal processing. One advantage of addition of the acid after, rather than before or during hydrothermal processing, is significantly less acid degradation occurs and so less acid is used in the process without a significant decrease in yield. In addition, acidification following hydrothermal processing results in a final product having in fewer impurities.

The acidified product may be held at a temperature of between about 40 degrees C and about 150 degrees C, between about 40 degrees C and about 70 degrees C, between about 70 degrees C and about 100 degrees C, between about 100 degrees C and about 130 degrees C, or between about 130 degrees C and about 150 degrees C. In other embodiments, the acidified product is heated to about 40 degrees C, about 45 degrees C, about 50 degrees C, about 55 degrees C, about 60 degrees C, about 65 degrees C, about 70 degrees C, about 75 degrees C, about 80 degrees C, about 85 degrees C, about 90 degrees C, about 95 degrees C, about 100 degrees C, about 105 degrees C, about 110 degrees C, about 115 degrees C, about 120 degrees C, about 125 degrees C, about 130 degrees C, about 135 degrees C, about 140 degrees C, about 145 degrees C, or about 150 degrees C. The hold time may range from 1 minute to about 240 minutes, from 1 minute to 45 minutes, from 1 minute to about 5 minutes, from 5 minutes to about 10 minutes, from about 10 minutes to about 50 minutes, from 15 minutes to about 45 minutes, from about 20 minutes to about 40 minutes, or from about 25 minutes to about 35 minutes. In certain embodiments, the hold time may range from 0 minutes (no hold time) to about 1 minute, about 5 minutes, about 20 minutes, about 30 minutes, about 45 minutes, about 60 minutes, about 120 minutes or about 240 minutes. In other embodiments, the hold time is less than 5 minutes, about 1 minute, about 5 minutes, about 10 minutes, about 15 minutes, about 20 minutes, about 25 minutes, about 30 minutes, about 35 minutes, about 40 minutes, about 45 minutes, about 60 minutes, about 90 minutes, about 120 minutes, about 150 minutes, about 180 minutes, about 210 minutes, or about 240 minutes. During the hold period, the acidified product may optionally be mixed. Any method of mixing known in the art, including those discussed herein, may be used. Alternatively, the acidification may be achieved using an on-line mixer with no hold time.

Following the acid treatment, at least one solvent may be added to the acidified product to produce a solvent extraction composition. Optionally, prior to the addition of solvent, the pH of the material is determined and if necessary the pH adjusted that which existed prior to heating. In one embodiment, an amount of solvent approximately equal in volume to the volume of water present in the acidified product is added to produce a solvent extraction composition. In other embodiments the ratio of solvent to water in the acidified product is 0.1:1, 0.2:1, 0.3:1, 0.4:1, 0.5:1, 0.6:1, 0.7:1, 0.8:1, 0.9:1, 1.1:1, 1.2:1, 1.3:1, 1.4:1 or 1.5:1. Any solvent suitable for the extraction of oleaginous compounds may be used, including, but not limited to acetonitrile, ethanol, methyl-t-butyl ether (MTBE), methyl ethyl ketone (MEK), propanol, iso propyl alcohol (IPA), methanol, cyclohexane, heptane, toluene (methylbenzene), chloroform (trichloromethane), methylene chloride (dichloromethane) and methyl isobutyl ketone (MIBK). The solvent can be a polar solvent, a non-polar solvent, or a combination of polar and non-polar solvents. In one embodiment, any organic solvent with a low solubility in water or which is sparingly soluble in water, but in which lipids and other oleaginous compounds are soluble or substantially soluble can be used. In another embodiment, the solvent is one which is immiscible in water, but one in which lipids and other oleaginous compounds are miscible. Non-limiting examples of suitable solvents include hexane, cyclohexane, heptane, toluene (methylbenzene), chloroform (trichloromethane), methylene chloride (dichloromethane) and methyl isobutyl ketone (MIBK). Suitable solvents can be used alone or in combinations. In one embodiment, the ratio of biomass to water to solvent is 1:10:10. In other embodiments, the ratio of biomass to water to solvent is ratios are 1:1:1, 1:2:2, 1:3:3, 1:4:4, 1:6:6, or 1:8:8 The solvent extraction composition is heated in a closed extraction vessel to an extraction temperature between about 20 degrees C and about 150 degrees C, between about 90° C., and about 150° C., between about 100 degrees C and about 140 degrees C, between about 110 degrees C and about 130 degrees C, between about 50 degrees C and about 90 degrees C, between about 60 degrees C and about 80 degrees C, or between about 65 degrees C and about 75 degrees C. In other embodiments, the solvent extraction composition is heated to an extraction temperature of about 20 degrees C, about 25 degrees C, about 30 degrees C, about 35 degrees C, about 40 degrees C, about 45 degrees C, about 50 degrees C, about 55 degrees C, about 60 degrees C, about 65 degrees C. about 70 degrees C, about 75 degrees C, about 80 degrees C, about 85 degrees C, about 90 degrees C, about 95 degrees C, about 100 degrees C, about 105 degrees C, about 110 degrees C, about 115 degrees C, about 120 degrees C, about 125 degrees C, about 130 degrees C, about 135 degrees C, about 140 degrees C, about 145 degrees C or about 150 degrees C. The solvent extraction composition is held at the extraction temperature for between about 1 minute and about 240 minutes, between about 10 minutes and about 50 minutes, between about 15 minutes and about 45 minutes, between about 20 minutes and about 40 minutes, or between about 25 minutes and about 35 minutes. In other embodiments, the solvent extraction composition is held at the extraction temperature for about 5 minutes, about 10 minutes, about 15 minutes, about 20 minutes, about 25 minutes, about 30 minutes, about 35 minutes, about 40 minutes, about 45 minutes, about 50 minutes, about 55 minutes, about 60 minutes, about 90 minutes, about 120 minutes, about 150 minutes, about 180 minutes, about 210 minutes, or about 240 minutes. As discussed above, as the temperature increases, the pressure within the extraction vessel also increases. The pressure within the extraction vessel need not held at any particular level, but is maintained such that the liquids in the extraction vessel do not vaporize (undergo a phase change). During the process the solvent extraction composition is optionally mixed. If mixing is utilized it can be intermittent or constant. The mixing can be accomplished by any method known in the art. In one embodiment, mixing is accomplished using an impeller, rotor or paddle. In another embodiment, mixing is achieved by use of a pump. In some embodiments, a combination of mixing methods is used, for example, a pump in combination with an impeller. Other methods of mixing the feedstock will be readily apparent to those of skill in the art.

After the solvent extraction composition has been held at the extraction temperature for the desired period of time, the mixing (if used) and heating is discontinued and the organic phase or phases separated from the aqueous phase. Separation of the organic and aqueous phases can take place in the extraction vessel or the solvent extraction composition can be transferred to another vessel. In one embodiment the pressure in the extraction vessel is lowered to atmospheric pressure. In one embodiment, the solvent extraction composition is allowed to cool to a temperature between the extraction temperature and ambient temperature.

Any suitable method of achieving phase separation can be used. In one embodiment, separation between the organic and aqueous phases is achieved by centrifugation, either batch or continuous. Methods of separating liquid phases by centrifugation are well known in the art. In one embodiment, phase separation is achieved using a stacked disc centrifuge. In another embodiment, phase separation is achieved using a decanter centrifuge. In still another embodiment, gravity separation is used. In this embodiment, the solvent extraction composition is allowed to stand without mixing for a period of time to allow for separation into phases. It is also possible to combine centrifugation with gravity separation. For example and without limitation, gravity separation can be used to separate the liquid and particulate phases, and then the liquid phase further separated into the aqueous and organic phases using centrifugation.

Regardless of the method used, typically the solvent extraction composition will separate into at least an aqueous phase and an organic phase or miscella containing the oleaginous compound(s) or oil. In some embodiments, there may be at least three phases, a particulate phase, an aqueous phase and an organic phase or miscella. When mixtures of solvents are used, there may be more than one organic phase present. In addition, in some embodiments there may be an emulsion phase between the aqueous phase and the organic phase(s). As part of the separation process, the organic phase(s) is removed from the aqueous phase and, if present, the particulate phase. When gravity separation or batch centrifugation is used, the miscella can be removed by any method that results in minimal re-mixing of the phases. For example, and without limitation, the miscella can be removed by pouring, pumping, gravity flow or siphoning. When gravity separation is used, the removal of the miscella can be continuous or intermittent. In continuous gravity separation, solvent extraction composition is continuously added to the separation vessel and an equal amount of miscella continuously removed. When continuous centrifugation is used, the separated phases are continuously removed from the centrifuge and collected. The collected phases from continuous centrifugation can be subjected to further separation steps, such as additional centrifugation, if so desired.

Optionally, the separated aqueous phase is returned to a solvent extraction vessel and a volume of fresh solvent is added to produce a secondary solvent extraction composition.

The fresh solvent can be solvent recovered from previous extractions, new solvent or a combination of new and recovered solvent. Thus, in some embodiments fresh solvent contains less than 10%, less than 5%, less than 2%, less than 1%, less than 0.5%, less than 0.25% or less than 0.1% of material from the extracted biomass. In one embodiment, the volume of fresh solvent added is equal to the volume of the aqueous phase. In another embodiment, the volume of fresh solvent added is equal to the volume of the organic phase removed from the separated aqueous phase. The secondary solvent extraction composition is subjected to the solvent extraction and phase separation processes described above. This re-extraction of the aqueous phase and/or residual biomass can be carried out several times, for example 2 times, 3 times, 4 times, 5 times, 6 times or more. In one embodiment, a counter current system is used in which the organic phase or miscella from the re-extraction of the aqueous phase is used to provide some or all of the solvent in the first extraction.

The miscella obtained from the solvent extraction is treated to separate the solvent from the oleaginous compound(s). In one embodiment, solvent removal is by way of distillation. In this embodiment, the miscella is heated to a temperature sufficient to cause vaporization of the solvent, but lower than the vaporization temperature of the oleaginous compound(s) of interest. The vaporized solvent is recovered by condensation and collection. In one embodiment, the recovered solvent is reused in the solvent extraction process.

Following solvent removal, the oleaginous compound may be further concentrated by the use of one of more additional solvent removal processes. In one embodiment, such further concentration is achieved by a secondary distillation, adsorption, and/or centrifugation.

It should be appreciated that solvent extraction following hydrothermal treatment and acidification is optional. Thus, in some embodiments, the aqueous and organic phases may be separated using any of the method described herein without the use of a solvent. For example and without limitation, following hydrothermal treatment, with or without acidification, the treated material can be allowed to separate into at least an aqueous and an organic phase without the use of a solvent.

Analytical Methods

The analytical methods used for the algae oil feeds and the upgraded products discussed herein are those described in detail in Provisional Patent Application Ser. No. 61/547,391, filed Oct. 14, 2011, (incorporated herein), and with reference to data shown in Provisional Patent Application Ser. No. 61/521,687, filed Aug. 9, 2011 (incorporated herein). Boiling points and boiling distribution curves were obtained by Simulated Distillation ASTM D7169, wherein data is presented in mass percent boiling at a given temperature. Compositional analysis (compound groups and types) were obtained by HT GC-MS, including advanced and/or specially-modified methods and apparatus, wherein the data is reported in area percent. Elemental analysis was obtained by using a Perkin Elmer 240 Elemental Analyzer for CHNS/O, in current state-of-the-art methods related to ASTM D5291 (for C, H, and N) and ASTM D1552 and D4239 (for S), as are understood by those of skill in the art.

Many of the crude algae oils of this disclosure may be described as having a broad boiling range, for example, approximately 300-1350 degrees F true boiling point. It may be noted that the heavy fraction in the boiling point distribution is usually reported as 1020 degrees F+, as this is a conventional refinery vacuum distillation tower cut-point between "distillable" material and "non-distillable" material. The SIMDIST boiling point curves of this disclosure, including the Provisional Patent Application Ser. Nos. 61/547,391, filed Oct. 14, 2011, and 61/521,687, filed Aug. 9, 2011, incorporated herein, allow description of the 1020 degrees F+ material in more detail, for example, by estimating the 1020-1200 degrees F fraction, the 1200-FBP fraction, and the small portion above the FBP that is "non-detectable" or "non-distillable" even by SIMDIST. From the Provisional Patent Application Ser. No. 61/521,687, filed Aug. 9, 2011. SIMDIST boiling curves, one may see that certain crude algae oils contain a 1020-1200 degrees F fraction in the range of about 10-18 mass %, a 1200-FBP fraction in the range of about 8-15 mass %, and a portion that is non-detectable/non-distillable by SLMDIST in the range of about 2-5 mass %. Thus, the SIMDIST data in this disclosure, including those in Provisional Patent Application Ser. No. 61/521,687, filed Aug. 9, 2011, may be described as including compounds up to about C-100 and having boiling points up to about 1350 degrees F, or, in other words, providing a boiling point curve of percent off (mass fraction) versus temperature up to about 1350 degrees F. This translates to the SIMDIST equipment and methods used and described herein as providing data representing over about 95 percent of the material in the crude algae oil, but not representing the last few percent of the material, for example, about 2-5 mass % of the material.

The HT GC-MS procedures and equipment used to obtain the data in this disclosure provide spectral/chromatogram data representing a large portion, but again not all, of the crude algae oil. The HT GC-MS spectral/chromatogram data represents the crude algae oil portion boiling in a range of IBP to about 1200 degrees F, or, in other words, the entire crude algae oil except for approximately the 1200-FBP fraction and the SIMDIST-non-detectable material over the final boiling point. By again referring to the 1200 degrees F cut point of the SIMDIST curves in Provisional Patent Application Ser. No. 61/521,687, filed Aug. 9, 2011, one may describe the portion of the crude algae oil represented by the HT GC-MS spectra/chromatogram as about 80-90 mass percent of the crude oil.

Of the total peak area of the crude algae oil HT GC-MS chromatograms in this disclosure, including those in Provisional Patent Application Ser. No. 61/521,687, filed Aug. 9, 2011, about 50-75 percent of the peak area may be specifically identified and named. This means that the chromatogram is the "fingerprint" of about 80-90 mass percent of the crude algae oil, and about 50-75 percent of the fingerprint total peak area may be specifically named and categorized by compound type/class.

By this same approach, one may see from distillation curves and HT GC-MS data for upgraded algae oil products of this disclosure and Provisional Patent Application Ser. Nos. 61/547,391, filed Oct. 14, 2011, and 61/521,687, filed Aug. 9, 2011, incorporated herein, that the upgraded algae oil products typically are lighter in boiling point than the crude algae oil, containing less 1020 degrees F+ material and less 1200 degrees F+ material. Therefore, the SIMDIST curves represent about 98-100 mass percent of the upgraded algae oil products, and the HT GC-MS chromatogram total peak area represents a higher percentage (compared to that of the crude algae oil) of the upgraded algae oil products, for example, about 90-100 mass percent. Lastly, about 70-95 area percent of the total peak area of the upgraded oil product chromatogram is identifiable.

It should be noted that the crude algae oils discussed herein, and those for which analyses are shown in the Tables and Figures, are described in terms of mass percents boiling at given temperatures, area percents of compounds/compound groups, and weight percents of elements. Boiling points and boiling distribution curves were obtained by Simulated Distillation ASTM D7169, wherein data is presented in mass percent boiling at a given temperature. Compositional analysis (compound groups and types) were obtained by HT GC-MS, wherein the data is reported in area percent. Elemental analysis (EA) methods are known in the art; the EA data in this document were obtained by using a Perkin Elmer 240 Elemental Analyzer for CHNS/O in a method related to ASTM D5291 for C, H, and N, and to ASTM D1552 and D4239 for S.

The terms "area percent" and "area %" in this document, therefore, refer to peak area % as measured by HT GC-MS, wherein the HT GC-MS results take the form of a "fingerprint" of peaks indicating the composition of the analyzed sample. As will be understood by those of skill in the art, the peak(s) in the fingerprint corresponding to certain compounds/compound types may be identified and an area of those peak(s) calculated as a percentage of the total peak area for the sample.

It should be noted that HT GC-MS is currently used for most of the analyses described herein, and therefore for most statements defining embodiments of the disclosure, area percent is used as the unit for the compound group/class analyses. However, there may be calculational methods developed and refined in the future that allow the HT GC-MS data to be converted to weight percent or mass percent values. The literature on this topic suggests that weight percent or mass percent of the compounds of GC-MS peaks in most cases will be within +/−10 percent of the area percent numbers. Also, alternative analysis methods may be developed in the future, wherein the output of which may be weight percent or mass percent values. Therefore, in certain embodiments, the area percent numbers and ranges reported and claimed in this document may be used to describe the certain embodiments, with "area percent" being replaced with "weight percent" or "mass percent".

Alternative additional analytical techniques may be used in the future to characterize extracted algae oils according to embodiments of the disclosure. For example, the additional techniques may include other mass spectrometric (high resolution, tandem mass spectrometry, and appropriate ionization methods), chromatographic (gas chromatography, liquid chromatography, supercritical fluid chromatography, etc) or spectroscopic (FTIR, NMR, Raman, etc) means of analysis.

The HT GC-MS methods used to analyze the extracted crude algae oils of this document were generally as follows. Sample pretreatment (2%) was done with 0.1 g sample being measured and dissolved in 10 mL $CS_2$ (carbon disulfide), stored in the a refrigerator. A solvent blank run was performed in between as negative control. Chromatograms were integrated and peak spectra (TIC) compared against the NIST08 and Wiley 9 library. Identified peaks were sorted according to the following compound classes: hydrocarbons—saturated; hydrocarbons—unsaturated; naphthenes and aromatics; aromatics containing nitrogen; acid amides; nitriles; fatty acids; oxygen compounds (non fatty acids); sterols/tocopherols; and sulfur compounds. Approximately 200 peaks per sample were typically detected, and roughly 50% of the peaks accounting for 75% to 90% of the total peak area were identified. The minimum match quality requirement was 80%.

More specifically, the analysis was performed using an Agilent 7890A gas chromatograph coupled with an Agilent 5975A (inert MSD) quadrupole mass spectrometer via a heated transfer line (300° C.). A 15 m×0.25 mm i.d. Zebron ZB-1HT Inferno™ (Phenomenex, Torrance, Calif.) fused-silica capillary column with 0.1 micron (micrometer) film thickness was used for the experiments described herein. The GC oven was held at 40° C. for 1 min and from there was programmed to reach 380° C. at a rate of 20° C./min. It remained at the upper temperature for 10 min. Helium was used as a carrier gas at a rate of 1.5 mL/min (constant flow). The mass spectrometer was operated in the full-scan mode, scanning from 20 to 800 Da, at a rate of 1.91 scans/s. The mass spectrometer was tuned in the electron ionization (EI) mode using the Agilent Autotune procedure with perfluorotributylamine (Agilent Technologies, New Castle, Del.) as calibration compound. The electron kinetic energy for the EI experiments was 70 eV. The ionization source temperature was 230° C. The temperature of the quadrupole analyzer was maintained at 150° C.

The HT-GCMS System and methods were modified, compared to conventional systems and methods, to accomplish the HT GC-MS analysis reported herein. The modifications comprise the following equipment and method adaptations.

Samples were introduced into the gas chromatograph via a cold, vacuum-tight, nondiscriminating injector (Cooled Injection System-CIS 4 PTV, Gerstel, Germany). The injector temperature was programmed from 10 to 400 degrees C at a rate of 12 degrees C/s. The injector temperature was maintained at 400 degrees C for 3 min. Dilute solutions (1 microliter aliquots) of samples (~2 wt % in $CS_2$) were introduced into the injector with a 7683B Series Agilent auto sampler. The split ratio was 10:1. Peaks in the chromatograms were defined and integrated using the Agilent system software. The nature of the individual compounds in the chromatograms was determined by matching the measured mass spectra against the reference spectra in the NIST08 and Wiley 9 libraries or by interpretation from first principles. The minimum library match quality was set to 80%.

Conventional split-splitless injection systems of GC/MS instruments are typically associated with sample discrimination at both the light and heavy boiling point ends. The light boiling compounds are partially lost due to their high volatility at the high split-splitless ratios used in hot injection systems (~250-275 degrees C) and high boiling compounds do not reach the analytical column due to their involatility at these moderate temperatures. Operating the injection system at higher temperatures is not recommended as organic compounds tend to thermally degrade at elevated temperatures.

To alleviate these problems, a cool on-column injection system (Gerstel Co., Germany) was acquired, the injection system permitting the injection of samples at low temperatures (e.g., <10 degrees C) without the adverse high pressure effects on the mass spectrometer associated with conventional on-column GC injectors. The system ensured the non-discriminating introduction of the light as well as the heavy compounds in algae oils without thermal degradation effects. Upon the initial injection of the sample at the low temperature, the injection system temperature was raised rapidly but in a very controlled manner to ensure the progressive volatization of all boiling compounds in the mixture. In that way, the specially-adapted injector permitted the introduction of compounds ranging from light to very heavy (e.g., B.P.>543 degrees C), which is required for the analysis of algae extracted oils and their upgraded oil products.

To further enable the elution of the heavy compounds from the column and the eventual detection by the mass spectrometer, the upper GC column temperature was set to reach 380 degrees C. The high helium carrier gas flow rate (1.5 mL/min) and the vacuum of the mass spectrometer created "effective" sub-ambient pressure conditions that correspond to significantly lower Atmospheric Equivalent Boiling Point (AEBP) temperatures. Under these conditions, the eluting molecules experience considerably reduced AEBP temperatures (i.e., boiling at lower temperatures than their atmospheric boiling points), which allows for the volatilization and analysis of very heavy molecules. These developed HT-GCMS methods and equipment enabled the detailed characterization of the extracted algae oils at the molecular level.

The above HT-GC-MS methods and equipment, therefore, have been important in analyzing and characterizing the extracted algae oils embodiments described herein. While these methods and equipment are the focus of at least one other patent application filed by Applicants, these methods and equipment are also disclosed herein in sufficient detail for one of skill in the GC-MS field to conduct the analyses.

Integration into a Refinery

There currently exists an extensive infrastructure for the transportation, refining, distribution and use of fuels obtained from geologic petroleum (fossil fuels). The ability of any alternative fuel source to utilize this existing infrastructure presents a distinct advantage in terms of rapid adoption and cost competitiveness. Presently, many alternative fuels are not suited for use in the existing petroleum infrastructure. For example, ethanol is incompatible with existing distribution networks due to its tendency to absorb water. In addition, existing gasoline engines require modification before they can burn fuels containing high amounts of ethanol.

The compositions disclosed herein have, among their many advantages, the ability to be a product or be made into a product that is substantially identical to geologic petroleum in that it is compatible with existing petroleum infrastructure and can be refined into the same classes of compounds as those obtained from the refining of fossil fuels. Thus, the disclosed compositions can be further refined into, among other things, jet fuel, aviation fuel (avgas), diesel fuel, gasoline, fuel oil and lubricating oil.

Jet fuels, such as Jet-A, Jet-A1 and JP-8, are a middle distillate that contains a mixture of straight and branched chain alkanes, aromatics and cycloalkanes having a chain length of between 10 to 14 carbons. Jet fuels are further characterized by a high energy density and the ability to remain liquid at very low temperatures.

Diesel fuel is composed of C8 to C21 hydrocarbons. Diesel is more energy dense than gasoline producing approximately 139,000 BTU/US gal when burned as opposed to 125,000 BTU/US gal for gasoline. Diesel fuel is characterized by its Cetane Index which is a measure of the fuel's propensity to auto-ignite under pressure. In the Cetane Index, cetane (n-hexadecane) is given a value of 100. Branched and aromatic molecules have a lower Cetane Index, but diesel fuel typically contains around 25% aromatic hydrocarbons to provide for good flow properties at lower temperatures.

Gasoline typically is made up of C4 to C12 alkanes, isoalkanes and aromatics. Gasoline is characterized by its Octane Number which is a measure of the fuel's ability to resist pr-detonation. In the Octane Number system, 2,2,4-trimethylpentane has an Octane Number of 100 while n-octane has a value of 0.

The term fuel oil encompasses a large variety of oils used in furnaces or boilers to generate heat and in internal combustion engines to generate power. Fuel oil is placed in 6 classes based on chain length and boiling point. Nos. 1 to 3 fuel oils (Nos. 1-3 diesel) contain hydrocarbons in the C9 to C20 range. Heavier fuel oils, Nos. 4-6, are made up of C12 to C70 hydrocarbons.

Aviation fuel (avgas) is typically 75 to 90% isooctane with the remainder being made up of toluene and C4 to C5 paraffins. The Octane rating of aviation fuel is generally equal to or greater than 100. Aviation fuel is very similar to gasoline used in automobiles, but is usually more uniform in composition and, unlike automotive gasoline, often contains lead as an anti-knock additive.

Full-boiling-range algae oils, fractions, or fraction blends may be fed to a refinery distillation section, and/or directly fed to one or more refinery units. Full-boiling-range algae oils, fraction, or fraction blends may be blended with other renewable oils and/or fossil petroleum fractions, for feeding to a refinery distillation section, and/or for direct feeding to one or more refinery units, as more fully discussed below.

It may be noted that many full-boiling-range extracted algae oils comprise a significant amount of material in each of multiple cuts traditionally produced in a crude distillation unit of a petroleum refinery. For example, certain algae oil embodiments comprise approximately 1.3 mass % 400-490 degrees F, 6.6 mass % 490-630 degrees F, 64.1 mass % 630-1020 degrees F and 27.5 mass % 1020 degrees F+ material. In the language of petroleum refining, the crude algae oil material is a mixture of kerosene/distillate (the 400-630 F boiling point range), gas oil (630 F-1020 F) and residuum (1020 F+). By altering the algae strains, growing conditions, and/or extraction conditions, it is expected that the composition of each of the 400-490 F, 490-630 F, 630-1020 F and 1020 F+ materials may be varied from these amounts, and it is expected that further processing in conventional refinery units will further vary these amounts and increase the quality of these cuts to match desired product specifications. Such crude algae oils, therefore, could be used as a feed to the front end of a petroleum refinery where it would be fractioned within the crude unit to distillate, gas oil and residuum and these corresponding fractions fed to further downstream units where they could be upgraded to fuels. Alternatively, the crude algae oil could be fed directly to one or more of a number of processing units downstream of the crude distillation units for upgrading (i.e. hydrotreaters, catalytic cracking units, hydrocracking units, cokers, etc.) to fuels. Also, the extracted algae oil could also be used to feed units separate from petroleum refineries such as pyrolysis and/or hydropyrolysis units for upgrading. Also, the extracted algae oil and fractions could be used directly as fuel blendstocks. For example, the naphtha cut (material boiling up to 430 F in the algae oil product) can be used for gasoline blending, the distillate cut (430-650 F) as a direct blendstock for diesel and/or jet fuels, the gas oil cut (650-1000 F) as a feed to a catalytic cracking unit and the residuum cut (1000 F+) as a blendstock for marine bunker fuels.

Many algae oil embodiments according to the disclosure have a boiling range similar to fossil petroleum gas oil (light vacuum gas oil plus heavy vacuum gas oil). This boiling range may be described as 300-1300 degrees F (true boiling point (TBP) by ASTM D7169 Simulated Distillation). Examples of boiling point distribution for certain algae oils hydrothermally extracted at 260-300 degrees C (500-572 degrees F) include the ranges of: 0-1 mass % in the IBP—260 degrees F fraction, up to 5 mass % in the 260-400 degrees F fraction, 1-6 mass % in the 400-490 degrees F fraction, 5-30 mass % in the 490-630 degrees F fraction, 35-65 mass % in the 630-1020 degrees F fraction, and 25-35 mass % in the 1020+ degrees F fraction. By changing algae oil strain, growing conditions, and/or hydrothermal treatment conditions, one may achieve algae oils of different boiling point distributions, for example, more severe conditions may produce algae oils containing higher distillate (400-490 degrees F) and gas oil (630-1020 degrees F) but much lower or no 1020 F+ material. Thus, a variety of full-boiling-range extracted algae oils may be produced from algae biomass, wherein "full-boiling-range" means the oleaginous material obtained from the extraction without subsequent distillation/fractionation. If distillation/fractionation is done after extraction, various fractions of the extracted algae oil may be obtained as desired, wherein the volume of a particular fraction will be dependent upon the boiling distribution of the full-boiling-range algae oil.

The novel oils are low in saturated hydrocarbon, and high in oxygen, nitrogen, and fatty acid content. Most embodiments are low in sulfur and triglycerides. For example, certain embodiments comprise:

a) less than 10 area % saturated hydrocarbons, more typically 0.1-5 area % saturated hydrocarbon, and even more typically 0.1-3 area % saturated hydrocarbons; and/or
b) greater than 5 area % Oxygen, and more typically 6-10 area % Oxygen; and/or
c) greater than 3 area % Nitrogen, and more typically 3.5-6 area % Nitrogen; and/or
d) greater than 15 area % fatty acids, and more typically 15-60 area % fatty acids, and even more typically 15-40 area % fatty acids; and/or
e) less than 2 area % Sulfur, and more typically less than 1.5 area % Sulfur; and/or
f) little or no triglycerides, for example, less than 1 area % and more typically less than 0.05 area % triglycerides; and/or
g) Hydrogen to Carbon molar ratios of greater than 1.5, and more typically 1.6-2.1; and/or
h) less than 10 area % aromatics, more typically 0.1-5 area %, and even more typically 0.1-3 area % aromatics; and/or
i) 0.1-2 area % nitriles; and/or
j) 1-15 area % amides; and/or
k) 1-10 area % Nitrogen compounds; and/or
l) 1-15 area % Oxygen compounds (other than fatty acids); and/or
m) over 5 area % sterols plus steroids, and more typically 8-15 area % sterols plus steroids (sterol content, however, appears to be a class of compounds that is sensitive to algae strain and some crude algae oils have exhibited little sterol content).

As may be understood from the "and/or" terminology above, embodiments of the disclosure may comprise one or more of the above characteristics a-m in any combination. However, many embodiments will comprise multiple of these characteristics in any combination, and typically will comprise more than half of these characteristics (7 or more), or more than three-quarters (10 or more) of these characteristics, in any combination.

The term "fatty acid" in the context of HT GC-MS results, includes both free fatty acids and esters of fatty acids, unless the fatty acids and esters are specifically reported as two separate groups. The amount of free fatty acids in the crude algae oils of the disclosure is believed to typically be very high compared to the amount of fatty acid esters, and the fatty acid esters are believed to be mainly methyl esters. The free fatty acids in many of the crude algae oil embodiments of the disclosure comprise those naturally-occurring in the algae and those produced by hydrolysis of glyceride compounds during extraction from the algae. Triglyceride and other glyceride compounds in algae depend on the algae strain and the growing conditions, for example, with triglyceride content being expected to be less than 20 area % except in some slow-growing algae, for example, or even less than 10 area % in many algae from which crude algae oil is extracted as described in embodiments of the disclosure. As mentioned above, many triglycerides and other lipids are hydrolyzed during the hydrothermal extraction, increasing fatty acid area % in the HT GC-MS fingerprint of the extracted algae oil. The fatty acid moieties may range, for example, from about 4 to about 30 carbon atoms, but typically 10 to 25 carbon atoms, and even more typically, 16 to 22 carbon atoms. The fatty acid moieties most commonly contain 1, 2, 3, or more double bonds (but typically fewer than six).

Therefore, one may describe the crude algae oils for most embodiments of the disclosure as being mainly aliphatic and containing many long, unsaturated straight-chain fatty acid moieties. Further, the algae oils of many of the embodiments may contain a wide range of other compounds, as evidenced by the wide range of peaks shown by HT GCMS, for example, sterols, carotenoids, tocopherols, fatty alcohols, terpenes, and others compounds. Many of the algae oil embodiments are primarily polar in nature, for example, due to containing heteroatom-containing (e.g., N, S, and O) compounds. Examples of such polar compounds include fatty acids, sterols, nitrogen-containing compounds, oxygen-containing compounds, amides, nitriles, wherein lower molecular weight compounds will be more polar than higher molecular weight compounds of the same polar class. Generally, the polar compound content of extracted algae oil may be estimated by considering what portion of the algae oil is not hydrocarbons (saturated hydrocarbons and unsaturated hydrocarbons) as measured by HT GC-MS, wherein the non-hydrocarbons are typically polar compounds including the heteroatom-containing compounds.

The following examples are intended to provide illustrations of the application of the present disclosure. The following examples are not intended to completely define or otherwise limit the scope of the disclosure. One of skill in the art will appreciate that many other methods known in the art may be substituted in lieu of the ones specifically described or referenced herein.

Example I

Figure 1B:
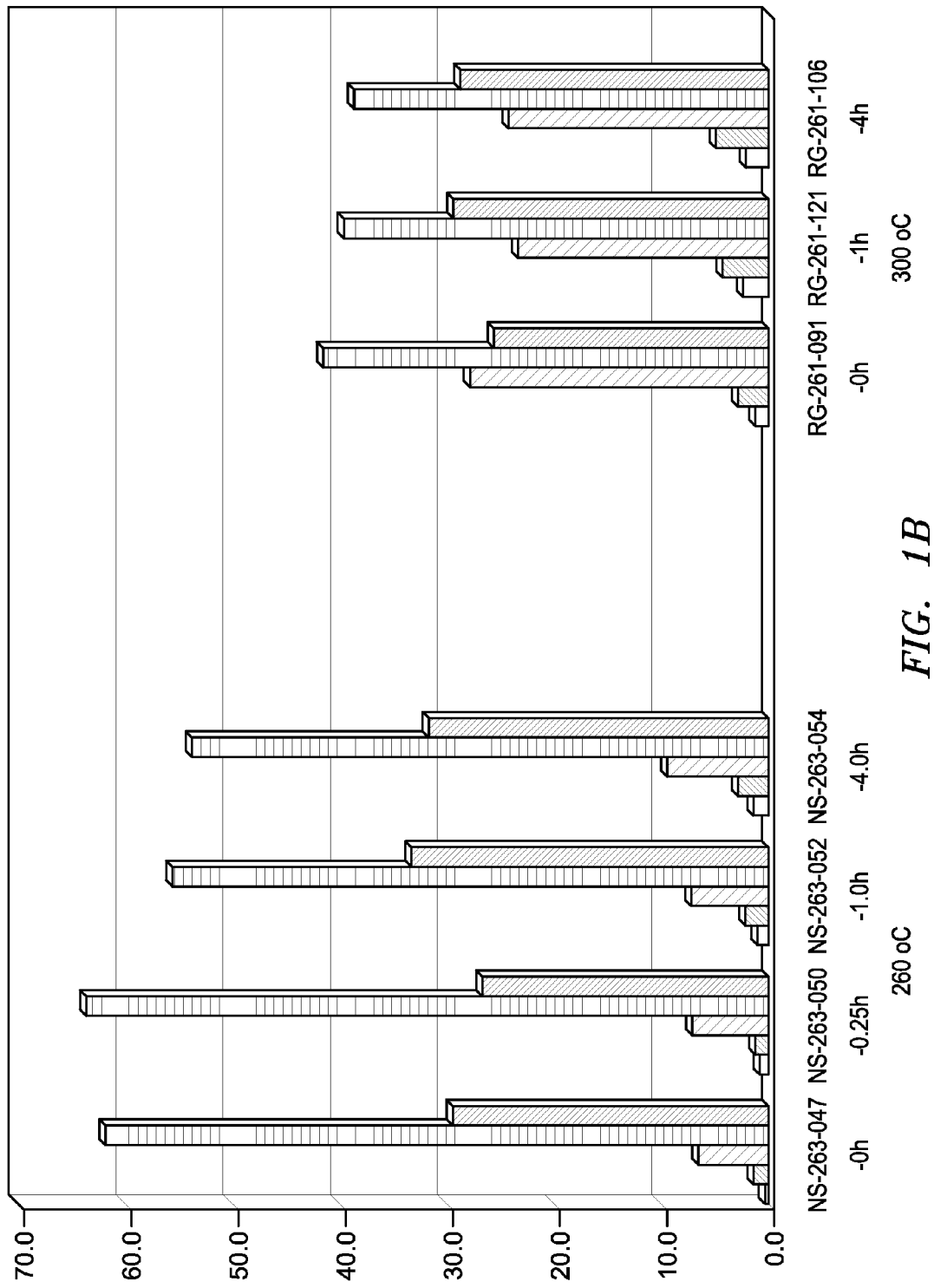
FIG. 1B is a bar graph of selected fractions of the algae oils of FIG. 1A. The y-axis is percent fraction mass. Each group of four bars is from left to right: 260-400 degrees F, 400-490 degrees F, 490-630 degrees F, 630-1020 degrees F, and greater than 1020 degrees F.

Several ASTM D7169 boiling point (BP) curves for crude algae oil embodiments are shown in FIG. 1A, and the BP distributions are summarized in FIG. 1B and Table 1A and Table 1B. These boiling point curves are generally representative of many "full-boiling range" algae oils according to the disclosure, wherein "full-boiling range" algae oils means the algae oil is the entire oleaginous composition obtained in extraction step (j) above, rather than a fraction thereof. Table 1A and Table 1B are shown below.

TABLE 1A

| | | Holding time (hours) | Fraction Mass Percent | | | | | |
|---|---|---|---|---|---|---|---|---|
| | Sample ID | | Initial-260° F. | 260-400° F. | 400-490° F. | 290-630° F. | 630-1020° F. | >1020° F. |
| 260° C. | NS-263-047 | 0 | 0 | 0.5 | 1.5 | 6.5 | 62.0 | 29.5 |
| | NS-263-050 | 0.25 | 0 | 1.0 | 1.3 | 7.1 | 63.8 | 26.8 |
| | NS-263-052 | 1 | 0 | 1.2 | 2.2 | 7.3 | 55.8 | 33.5 |
| | NS-263-054 | 4 | 0 | 1.5 | 3.0 | 9.5 | 54.1 | 31.9 |

TABLE 1A-continued

| | | Holding time (hours) | Fraction Mass Percent | | | | | |
|---|---|---|---|---|---|---|---|---|
| | Sample ID | | Initial-260° F. | 260-400° F. | 400-490° F. | 290-630° F. | 630-1020° F. | >1020° F. |
| 300° C. | RG-261-091 | 0 | 0 | 1.3 | 2.9 | 28.0 | 42.0 | 25.8 |
| | RG-261-121 | 1 | 0 | 2.4 | 4.4 | 23.5 | 40.0 | 29.7 |
| | RG-261-106 | 4 | 0 | 2.2 | 5.0 | 24.5 | 39.2 | 29.1 |

TABLE 1B

| | | Holding time (hours) | Cut point Mass Percent | | | | | |
|---|---|---|---|---|---|---|---|---|
| | Sample ID | | 260° F. | 400° F. | 490° F. | 630° F. | 1020° F. | >1020° F. |
| 260° C. | NS-263-047 | 0 | 0 | 0.5 | 2.0 | 8.5 | 70.5 | 29.5 |
| | NS-263-050 | 0.25 | 0 | 1.0 | 2.3 | 9.4 | 73.2 | 26.8 |
| | NS-263-052 | 1 | 0 | 1.2 | 3.4 | 10.7 | 66.5 | 33.5 |
| | NS-263-054 | 4 | 0 | 1.5 | 4.5 | 14.0 | 68.1 | 31.9 |
| 300° C. | RG-261-091 | 0 | 0 | 1.3 | 4.2 | 32.2 | 74.2 | 25.8 |
| | RG-261-121 | 1 | 0 | 2.4 | 6.8 | 30.3 | 70.3 | 29.7 |
| | RG-261-106 | 4 | 0 | 2.2 | 7.2 | 31.7 | 70.9 | 29.1 |

The algae oils were extracted from *Nannochloropsis* biomass by hydrothermal methods generally according to the extraction steps a-j listed above, wherein residence time was widely varied at two temperatures during the "heating and holding" extraction step (b). The temperature and holding times of extraction step (b) were varied to include four holding times (0, 0.25, 1, and 4 hours) at 260 degrees C and three holding times (0, 1, and 4 hours) at 300 degrees C. The pH of step (d) above was 4, and the solvent was heptanes. No flocculation step was performed. The analytical procedure for obtaining the BP distributions was as follows. ASTM D 7169; BP up to 720 degrees C (C10 to C100); standard preparation: prepared 0.5% Polywax 655 in $CS_2$ solution, then mixed with equal volume of D2887 SimDist standard. Sample pretreatment (2%), 0.1 g sample was measured and dissolved in 10 mL $CS_2$, stored in a refrigerator. A solvent blank run was performed in between as a negative control. Retention times are correlated to boiling points to obtain a calibration curve. Sliced Peak intensities represent the sample amount distilled=% Off.

The distillation yields at 1020° F. for all oils were between 68 and 74%. The most abundant fraction of the oils was in the 630-1020° F. BP range (VGO range), specifically 39-42% at a step (b) temperature of 300° C., and 54-64% at a step (b) temperature of 260° C. Vacuum residue (>1020° F.) ranged from 26% to 33.5%. A higher temperature caused a shift to lower boiling points. For example, the vacuum residue was found to be slightly lower at 300° C. than at 260° C., specifically the >1020° F. fraction was reduced by about 3% when the temperature was increased from 260 to 300° C. At the same time, the 630-1020° F. fraction was reduced by 15 to 20%, but the 490-630° F. fraction was increased by about 15% when increasing the temp from 260 to 300° C. An increase of residence time typically slightly increased all of the vacuum residue (>1020° F.), 260-400° F., 400-490° F., and 490-630° F. fractions, while it slightly decreased the 630-1020° F. fraction.

As may be seen in FIG. 1A and FIG. 1B and Table 1A and Table B, an increase in residence time caused a slight shift to lower boiling points, and this effect was more pronounced at the lower temperature. Still, all of these BP distributions are examples of full-boiling-range extracted algae oil according to certain embodiments of the disclosure. As mentioned elsewhere in this document, however, other full-boiling-range algae oils may be obtained that are significantly different from these examples. For example, vacuum residue (>1020 degrees F) content may range anywhere from 0 to 35 mass %, with extracted algae oils containing residue at the lower end of that range typically containing correspondingly higher amounts of distillate and/or gas oil.

Example II

Figure 2:
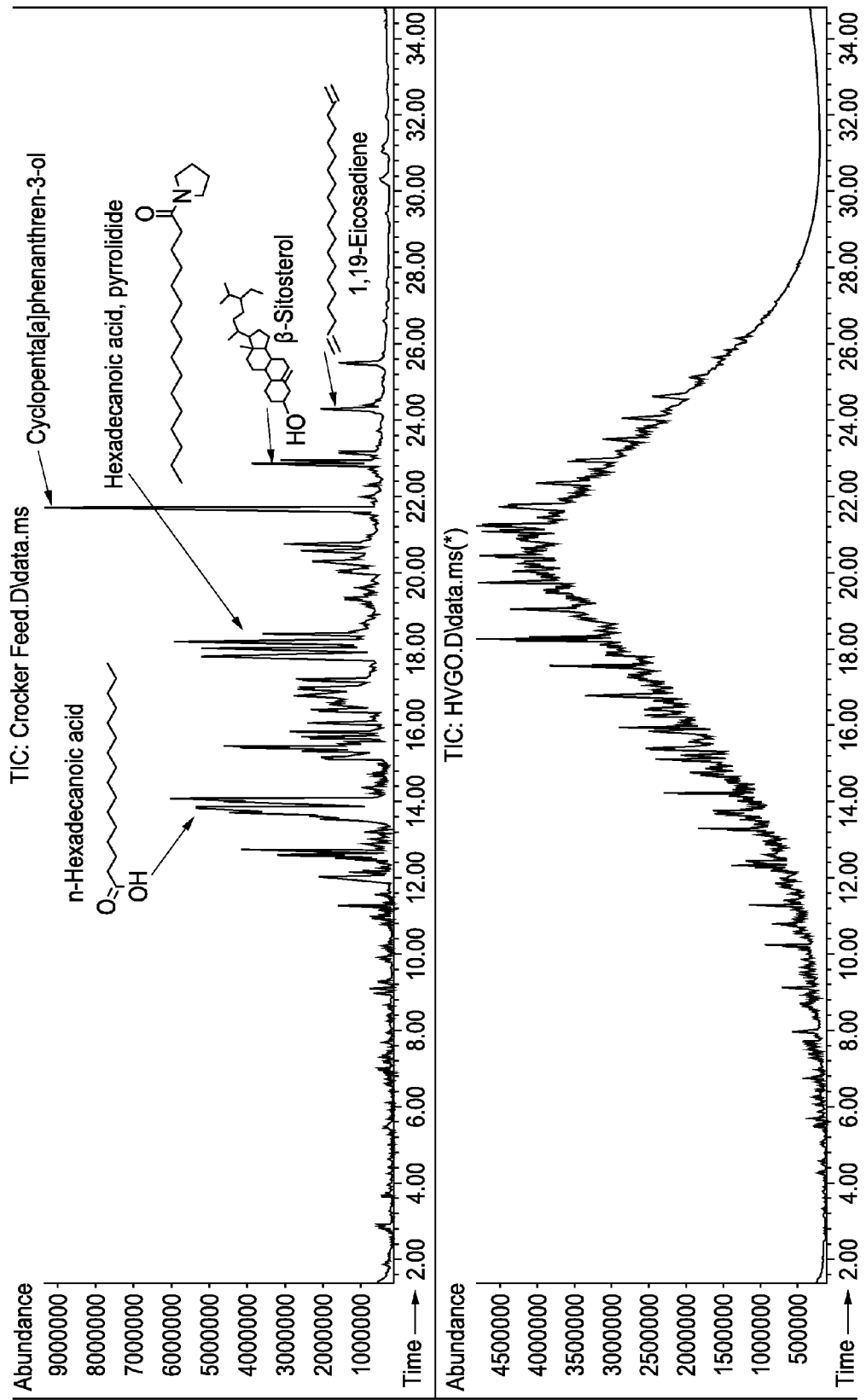
FIG. 2 includes HT GC-MS "fingerprints" of an algae oil in EXAMPLE II (top panel) according to another embodiment of the disclosure and a representative heavy vacuum gas oil (bottom panel), wherein the algae oil is substantially in the HVGO boiling point range. In these and all HT GC-MS fingerprints in the Figures of this disclosure, the x-axis is time and the y-axis of the fingerprints is abundance.

A GC fingerprint, and detailed compositional information, of another embodiment of the algae oil composition of matter are shown in FIG. 2. Algae oil was extracted from *Nannochloropsis* according to the above-listed hydrothermal treatment and solvent extraction steps. FIG. 2 compares this crude algae oil (top panel) to a HT GC-MS fingerprint and detailed compositional information of a HVGO fraction of a fossil petroleum crude (bottom panel). Table 2A, Table 2B, and Table 2C are shown below. Table 2A shows compound classes of the exemplary algae oil. Table 2B compares EA data of the exemplary algae oil to that of the heavy VGO. Table 2C shows compositional analysis of the heavy VGO.

TABLE 2A

| | algae oil (%) |
|---|---|
| saturates | 1.7 |
| olefins | 9.5 |
| aromatics | 1.3 |
| fatty acids | 26.1 |
| amides | 10.9 |
| N-aromatics | 2.7 |
| oxygenates | 7.9 |
| sterols | 9.1 |

TABLE 2B

| | algal oil | heavy VGO |
|---|---|---|
| wt % Carbon | 78.2 | 86 |
| wt % Hydrogen | 10.6 | 10.7 |

TABLE 2B-continued

|  | algal oil | heavy VGO |
|---|---|---|
| wt % Nitrogen | 4.1 | <1 |
| wt % Oxygen | 6.4 | <1 |
| wt % Sulfur | <1 | 2.3 |
| H/C ratio | 1.63 | 1.49 |

TABLE 2C

|  | HVGO (%) |
|---|---|
| saturates | 23.2 |
| monoaromatics | 19.0 |
| diaromatics | 22.2 |
| triaromatics | 9.2 |
| tetra-aromatics | 8.4 |
| penta-aromatics | 1.1 |
| thiopheno aromatics | 8.9 |

As may be understood from the many distinct peaks along a wide portion of the x-axis of the algae oil fingerprint, the crude algae oil contains a wide range of compounds, especially in comparison to the more uniform and "narrow" fingerprint of the HVGO. One may see in FIG. 2 the very different algae oil compound types compared to the HVGO, for example, saturates of 1.7% (peak area %) in the algae oil compared to 23.2% in the HVGO; aromatics of 1.3% compared to a total of 68.8%; and fatty acids of 26.1%, amides of 10.9%, and sterols of 9.1% compared to negligible amounts 0% for the HVGO. Note that the saturates and aromatics of the HVGO total 92%, with all other compounds, by difference, being only 8%.

Figure 3:
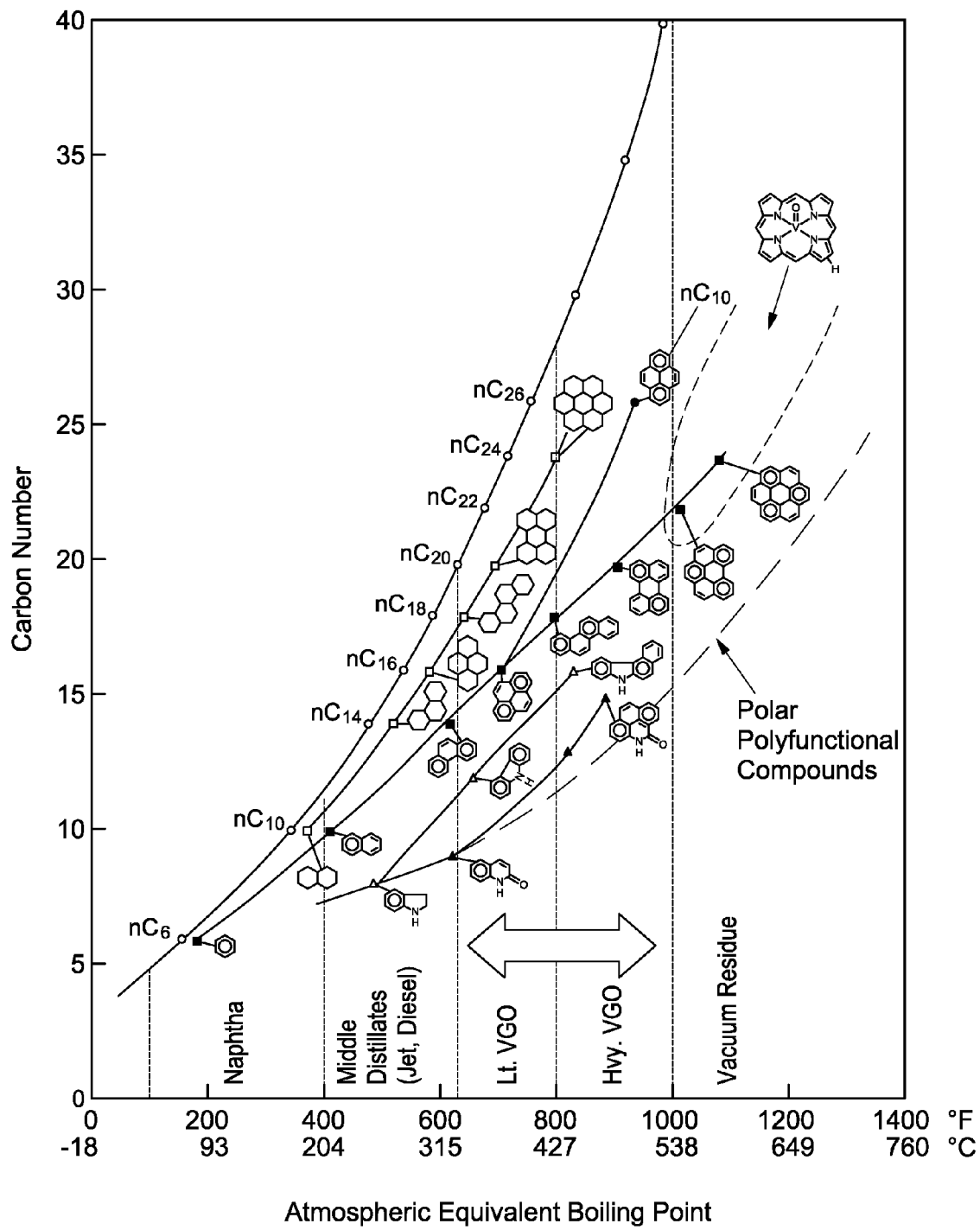
FIG. 3 is a Boduszynski Plot, of carbon number (y-axis) vs. atmospheric equivalent boiling point (AEBP, x-axis), which has been modified to include an indication (arrow) of the region on the plot where lie many algae oil embodiments of the disclosure, the algae oil being unusually polar in character compared to conventional fossil oils and vegetable oils.

FIG. 2 and Table 2B also shows the very different elemental analysis of the crude algae oil compared to the HVGO, for example, about the same hydrogen content but much less carbon content. The crude algae oil comprises 4.1% nitrogen and 6.4% oxygen, while the HVGO comprises very little of either nitrogen or oxygen. The crude algae oil contains little sulfur, on the other hand, while, on the other hand, the HVGO contains 2.3%. Table 2B shows the elemental compositions of the algae oil and HVGO of FIG. 2. The resulting H/C molar ratio of the algae oil is calculated to be 1.63 H/C molar ratio, compared to 1.49 for the HVGO. From these H/C molar ratios, one may note the highly aliphatic nature of the extracted algae oil, compared to the highly aromatic nature of the HVGO. FIG. 2 and Table 2B also show that the algae oil contains compound types with several heteroatoms and is more polar than the HVGO. Therefore, this and many other algae oil embodiments according to the disclosure may be described as containing higher amounts of heteroatom-containing compounds, compared to those in a typical HVGO. See, for example, the algae oil location on the Boduszynski Plot in FIG. 3, which has a high atmospheric equivalent boiling point range given its carbon number, which translates to the algae oil having a very polar composition.

Example III

Additional embodiments of the novel algae oils are described in Table 3A and Table 3D and in FIG. 4-FIG. 12. Table 3A and Table 3D list compositional and elemental analysis, by HT-GC-MS, of the additional algae oil embodiments. These algae oils were produced from various algae strains, specifically *Nannochloropsis, Scenedesmus, Spirulina*, and *Dunaliella*, and extracted by hydrothermal methods according to extraction steps (a)-(j) disclosed above. Step (b) of the extraction was performed using 30 minutes holding time at 300 degrees C, and steps f-j were performed with mixed heptanes solvent in some embodiments and MIBK solvent in other embodiments, as is apparent from the tables and figures. Table 3A, Table 3B. Table 3C. and Table 3D are provided below. Table 3B and Table 3C are described further below.

|  | algae strain | saturated hydrocarbons | unsaturated hydrocarbons | aromatics | nitrogen compounds | nitriles |
|---|---|---|---|---|---|---|
| Heptanes | *Spirulina* | 5.5 | 2.6 | 2.5 | 8.6 | 0.7 |
|  | *Dunaliella* | 1.2 | 5.8 | 3.7 | 8.1 | 0.0 |
|  | *Scenedesmus* | 3.0 | 9.9 | 2.5 | 4.2 | 0.0 |
|  | *Nannochloropsis* | 2.8 | 10.1 | 0.3 | 1.0 | 0.0 |
|  | Average | 3.1 | 7.1 | 2.3 | 5.5 | 0.2 |
| MIBK | *Spirulina* | 5.7 | 3.5 | 2.5 | 6.6 | 0.0 |
|  | *Dunaliella* | 3.0 | 7.0 | 2.7 | 6.2 | 0.0 |
|  | *Scenedesmus* | 2.9 | 11.0 | 2.2 | 4.7 | 0.6 |
|  | *Nannochloropsis* | 1.0 | 7.4 | 0.8 | 3.5 | 0.0 |
|  | Average | 3.2 | 7.2 | 2.1 | 5.3 | 0.2 |
| crude oils | Arabian light | 65.8 | 1.0 | 9.7 | 1.1 | 0.0 |
|  | Arabian extra-light | 62.7 | 0.6 | 13.4 | 0.4 | 0.0 |
|  | Arabian medium | 66.2 | 1.0 | 7.8 | 0.4 | 0.0 |
|  | Arabian heavy | 64.1 | 1.0 | 5.7 | 0.9 | 0.0 |
|  | Average | 64.7 | 0.9 | 9.2 | 0.7 | 0.0 |
| HVGO |  | 23.2 |  | 68.8 |  |  |
| jet fuel |  | 65.6 |  | 34.3 |  |  |
| bio-oils | *Camelina* oil | mostly triacylglycerides (TAGs) ~100% | | | | |
|  | Canola oil | mostly triacylglycerides (TAGs) ~100% | | | | |

|  | algae strain | amides | fatty acids/ esters | oxygen compounds | sterols/ steroids | unknown |
|---|---|---|---|---|---|---|
| heptane | *Spirulina* | 10.0 | 22.4 | 1.1 | 0.8 | 45.8 |
|  | *Dunaliella* | 13.7 | 22.7 | 1.9 | 3.4 | 39.5 |
|  | *Scenedesmus* | 1.1 | 35.5 | 6.9 | 4 | 32.9 |
|  | *Nannochloropsis* | 13.2 | 25.2 | 7 | 8.3 | 32.1 |
|  | Average | 9.5 | 26.5 | 4.2 | 4.1 | 37.6 |
| MIBK | *Spirulina* | 11.6 | 19.9 | 0.1 | 0.1 | 50.0 |
|  | *Dunaliella* | 14.5 | 15.5 | 1.4 | 2.3 | 47.4 |
|  | *Scenedesmus* | 6.8 | 26.9 | 5.7 | 2.9 | 36.3 |
|  | *Nannochloropsis* | 12.3 | 20.2 | 6.7 | 7.9 | 40.2 |
|  | Average | 11.3 | 20.6 | 3.5 | 3.3 | 43.5 |

-continued

| | | | | | | |
|---|---|---|---|---|---|---|
| crude oils | Arabian light | 0.0 | 0.0 | 1.2 | 0.0 | 100 |
| | Arabian extra-light | 0.0 | 0.0 | 0.8 | 0.0 | 100 |
| | Arabian medium | 0.3 | 0.0 | 2.3 | 0.0 | 100 |
| | Arabian heavy | 0.2 | 0.0 | 2.0 | 0.1 | 100 |
| | Average | 0.1 | 0.0 | 1.6 | 0.0 | 100 |
| HVGO | | | | | | 8.0 |
| jet fuel | | | | | | 0.1 |
| bio-oils | *Camelina* oil | \multicolumn{5}{c}{mostly triacylglycerides (TAGs) ~100%} | |
| | Canola oil | | | | | |

TABLE 3B

| | HVGO (area %) |
|---|---|
| Saturates | 23.2 |
| Monoaromatics | 19.0 |
| Diaromatics | 22.2 |
| Triaromatics | 9.2 |
| tetra-aromatics | 8.4 |
| penta-aromatics | 1.1 |
| thiopheno aromatics | 8.9 |

TABLE 3C

| | jet fuel A (area %) |
|---|---|
| saturates | 65.6 |
| olefins | — |
| aromatics | 34.3 |
| Oxygenates | — |

Table 3D show elemental analysis (weight percent), C is Carbon, H is Hydrogen, N is Nitrogen, S is Sulfur, and O is Oxygen.

| | algae strain | C | H | N | S | O * (by difference) |
|---|---|---|---|---|---|---|
| heptane | *Spirulina* | 77.6 | 10.6 | 5.3 | 1.4 | 5.1 |
| | *Dunaliella* | 79.2 | 10.6 | 4.3 | 1.6 | 4.3 |
| | *Scenedesmus* | 78.0 | 10.2 | 3.0 | 1.2 | 7.2 |
| | *Nannochloropsis* | 78.5 | 10.9 | 3.5 | 0.9 | 6.2 |
| | Average | 78.3 | 10.6 | 4.0 | 1.3 | 5.7 |
| MIBK | *Spirulina* | 73.0 | 9.5 | 6.9 | 0.0 | 9.9 |
| | *Dunaliella* | 75.2 | 9.3 | 5.8 | 1.1 | 8.5 |
| | *Scenedesmus* | 73.2 | 9.2 | 5.7 | 0.0 | 11.5 |
| | *Nannochloropsis* | 74.8 | 10.0 | 4.9 | 0.5 | 9.6 |
| | Average | 74.1 | 9.5 | 5.8 | 0.4 | 9.9 |
| crude oils | Arabian light | 84.9 | 13.2 | 0.3 | 2.3 | 0.0 |
| | Arabian extra-light | 84.7 | 13.5 | 0.3 | 1.2 | 0.4 |
| | Arabian medium | 84.8 | 12.7 | 0.4 | 3.7 | 0.0 |
| | Arabian heavy | 84.8 | 12.3 | 0.2 | 3.3 | 0.0 |
| | Average | 84.8 | 12.9 | 0.3 | 2.6 | 0.1 |
| HVGO | | 86.0 | 10.7 | 0.0 | 2.3 | 0.0 |
| jet fuel | | 86.2 | 12.3 | 0.0 | 0.0 | 0.0 |
| bio-oils | *Camelina* oil | 78.7 | 12.4 | 0.0 | 0.0 | 9.2 |
| | Canola oil | 77.6 | 13.5 | 0.0 | 0.0 | 7.8 |
| | Average | 78.1 | 12.9 | 0.0 | 0.0 | 8.5 |

Figure 4:
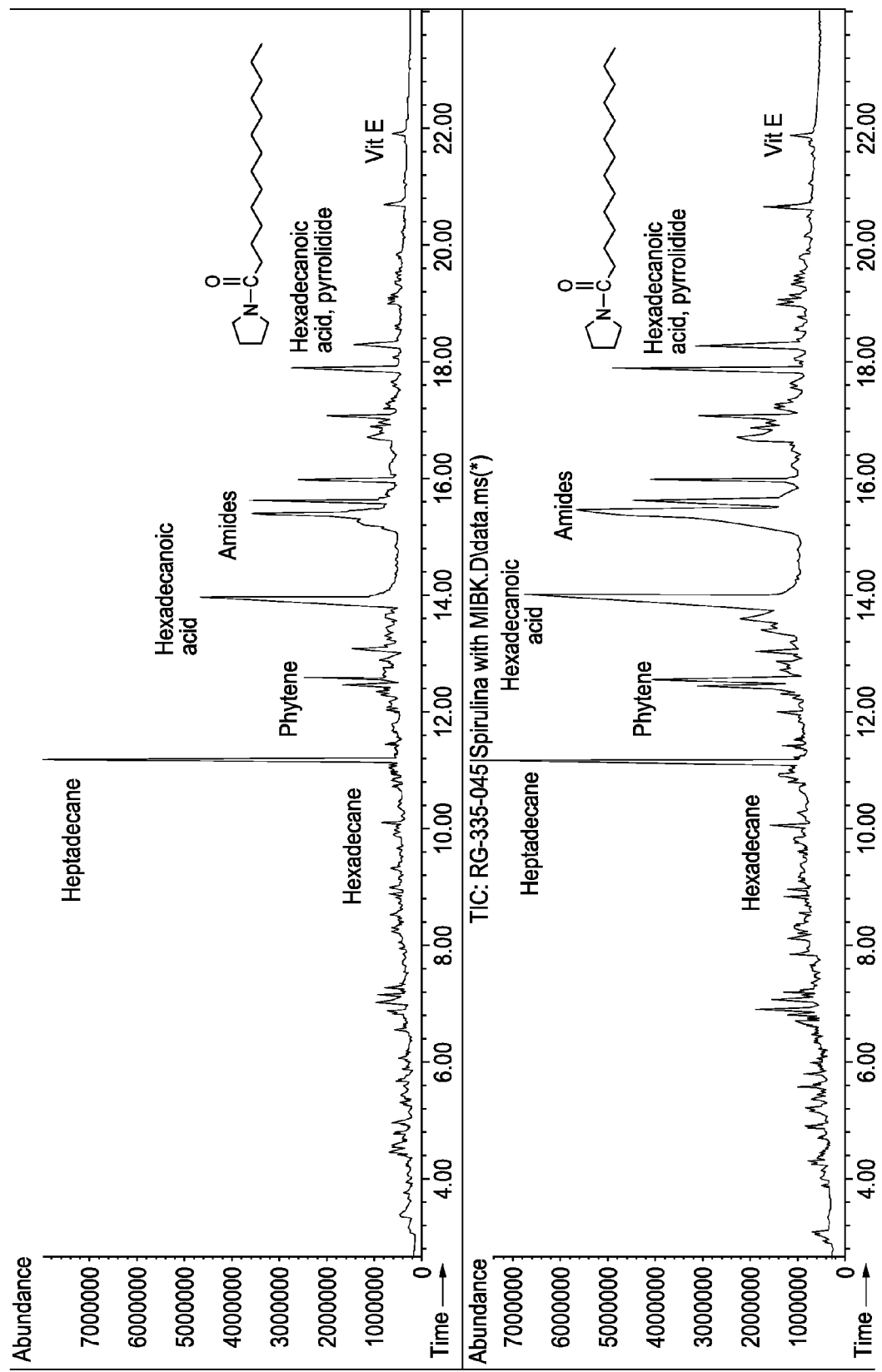
FIG. 4 compares HT GC-MS fingerprints of algae oils described in EXAMPLE III according to additional embodiments of the disclosure, extracted from *Spirulina* biomass using mixed heptanes as a solvent (top panel) and methyl isobutyl ketone (MIBK) as a solvent (bottom panel).
Figure 5:
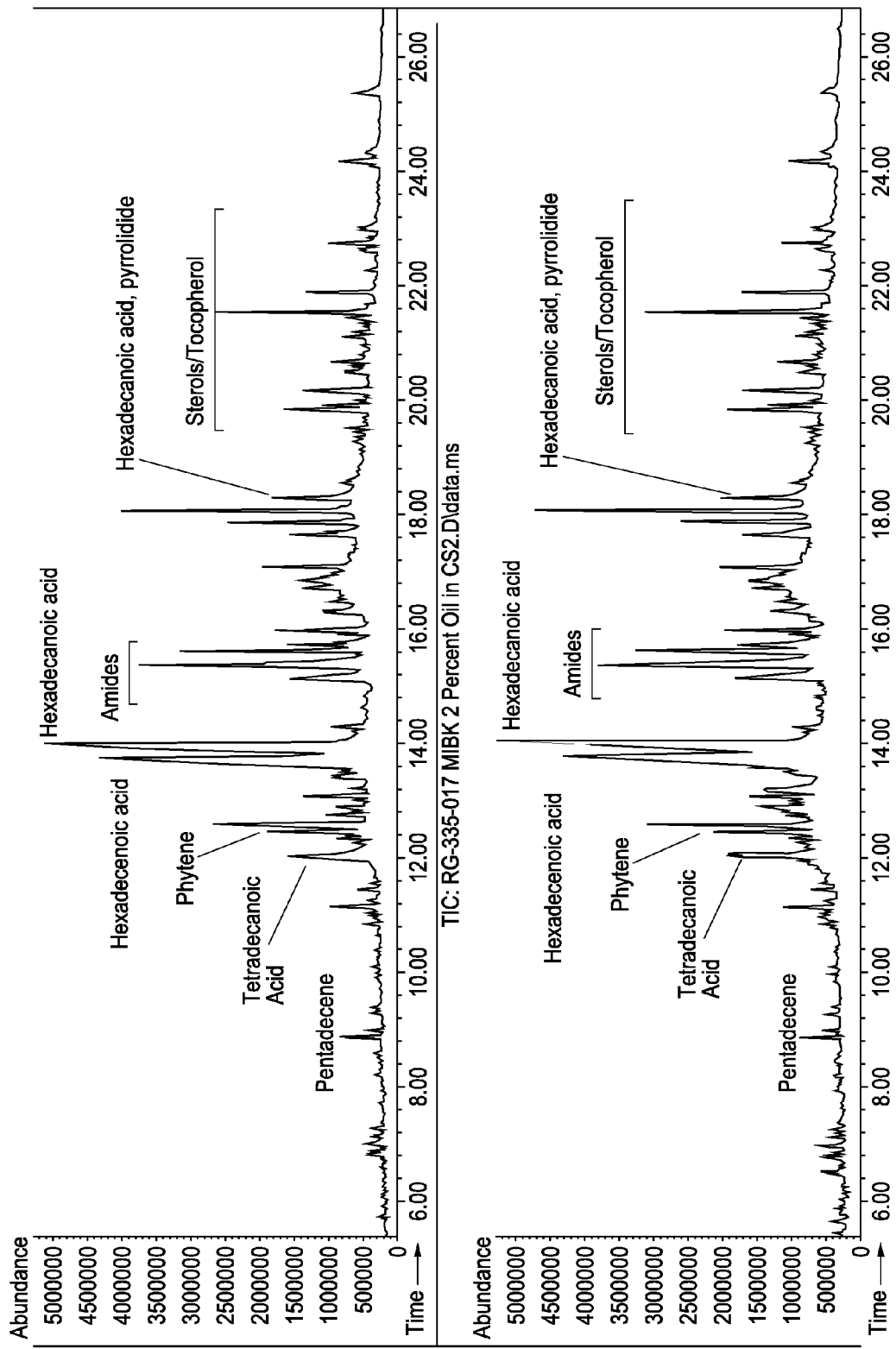
FIG. 5 compares HT GC-MS fingerprints of algae oils described in EXAMPLE III according to additional embodiments of the disclosure, extracted from *Nannochloropsis* biomass using heptanes as a solvent (top panel) and MIBK as a solvent (bottom panel).
Figure 6:
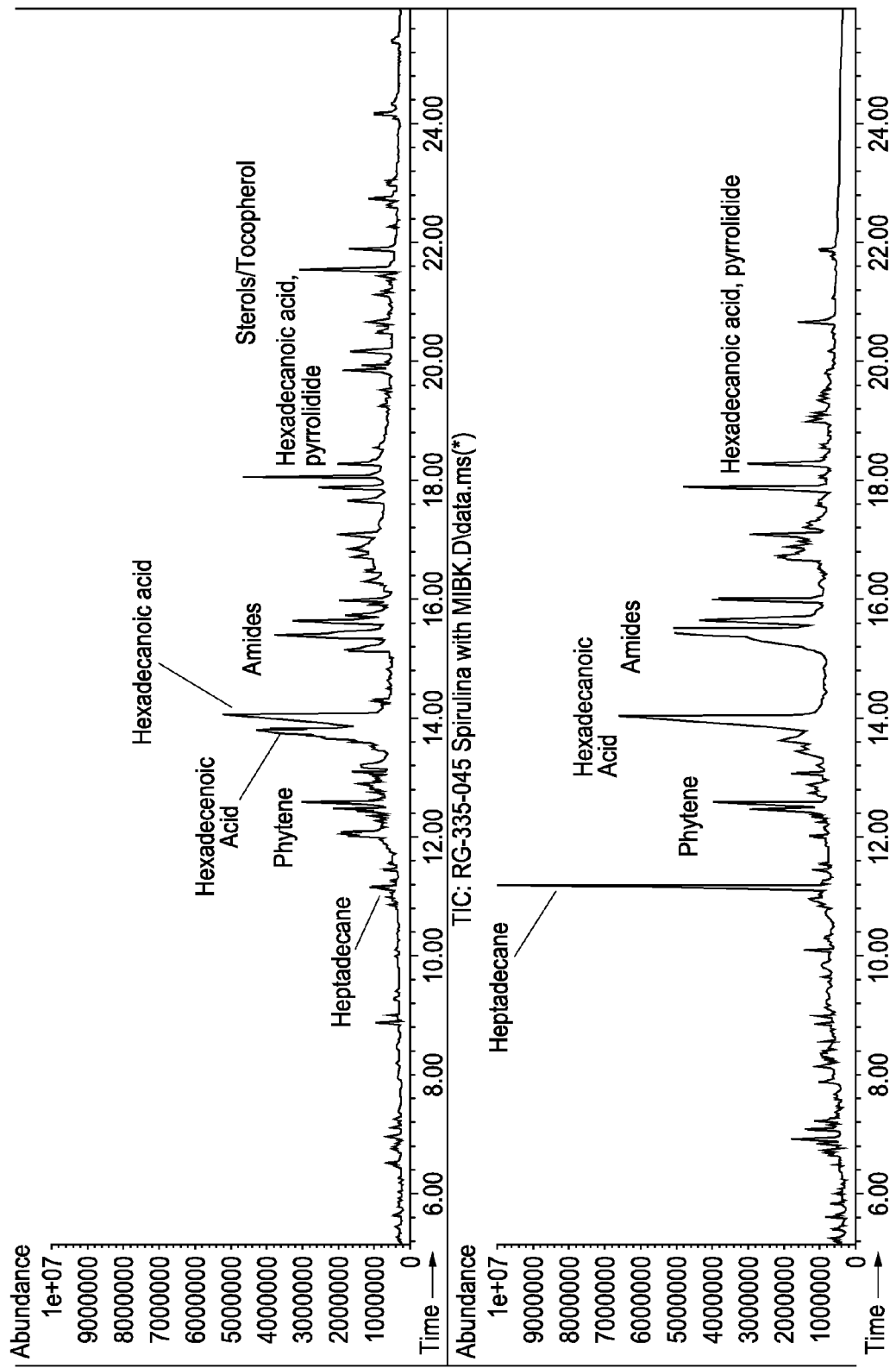
FIG. 6 compares HT GC-MS fingerprints of the algae-oils of FIG. 4 and FIG. 5 that were MIBK-extracted from *Nannochloropsis* (top panel) and *Spirulina* (bottom panel).
Figure 7:
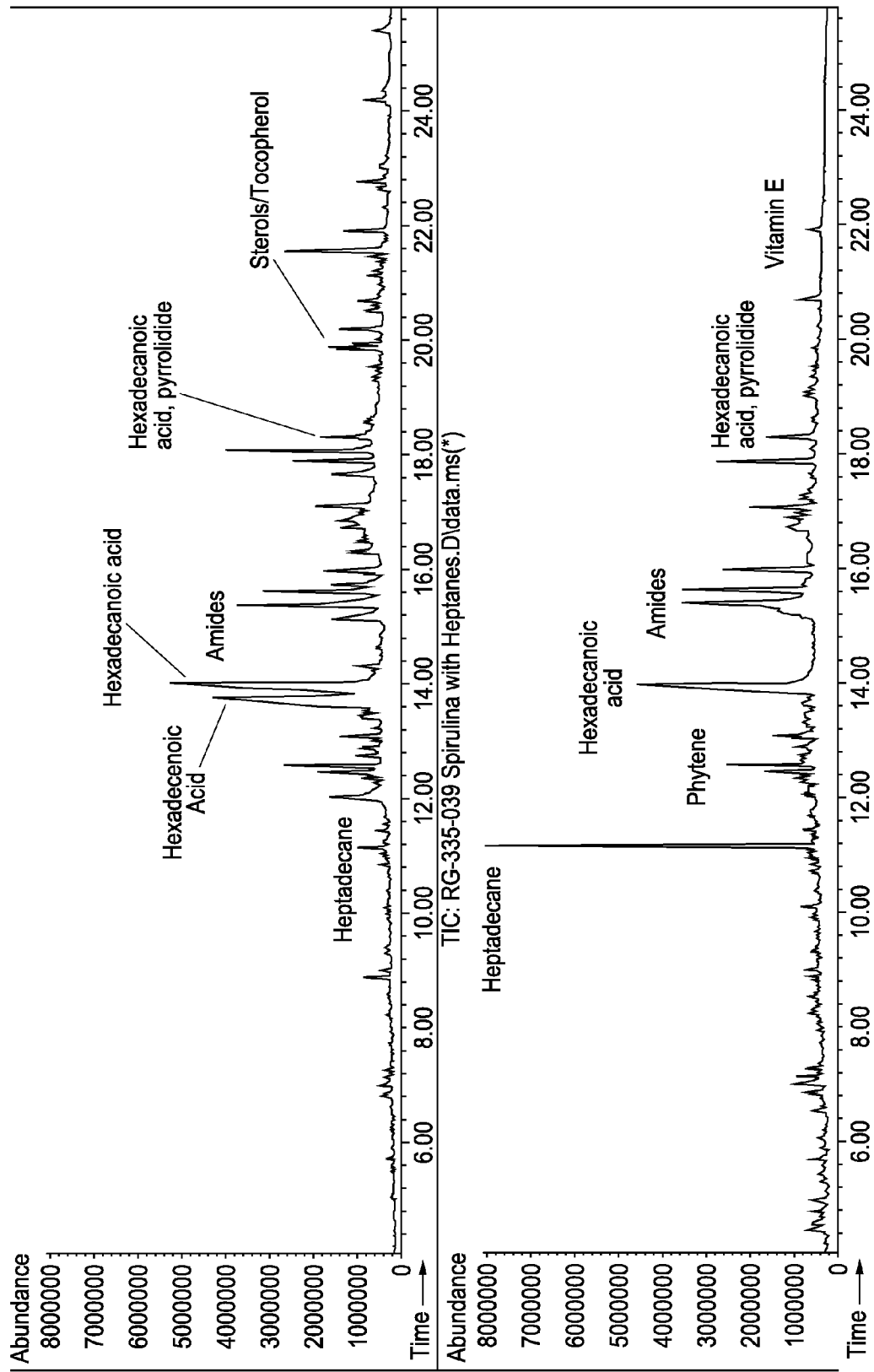
FIG. 7 compares HT GC-MS fingerprints of the algae-oils of FIG. 4 and FIG. 5 that were mixed-heptanes-extracted from *Nannochloropsis* (top panel) and *Spirulina* (bottom panel).

GC fingerprints of selected algae oil embodiments are shown in FIG. 4-FIG. 7 and emphasize the similarity of the algae oils extracted from a given strain even when different solvents are used. Specifically, FIG. 4 compares crude algae oil hydrothermally extracted from *Spirulina* biomass with heptanes (top) to crude algae oil extracted from the same biomass with MIBK (bottom). FIG. 5 compares crude algae oil hydrothermally extracted from *Nannochloropsis* biomass with heptanes (top) to crude algae oil extracted from the same biomass with MIBK (bottom). FIG. 6 illustrates algae oil hydrothermally extracted with MIBK solvent from *Nannochloropsis* (top) to algae oil extracted by the same method from *Spirulina* (bottom). FIG. 7 illustrates algae oil hydrothermally extracted with heptanes from *Nannochloropsis* (top) to algae oil extracted by the same method from *Spirulina* (bottom).

Figure 8:
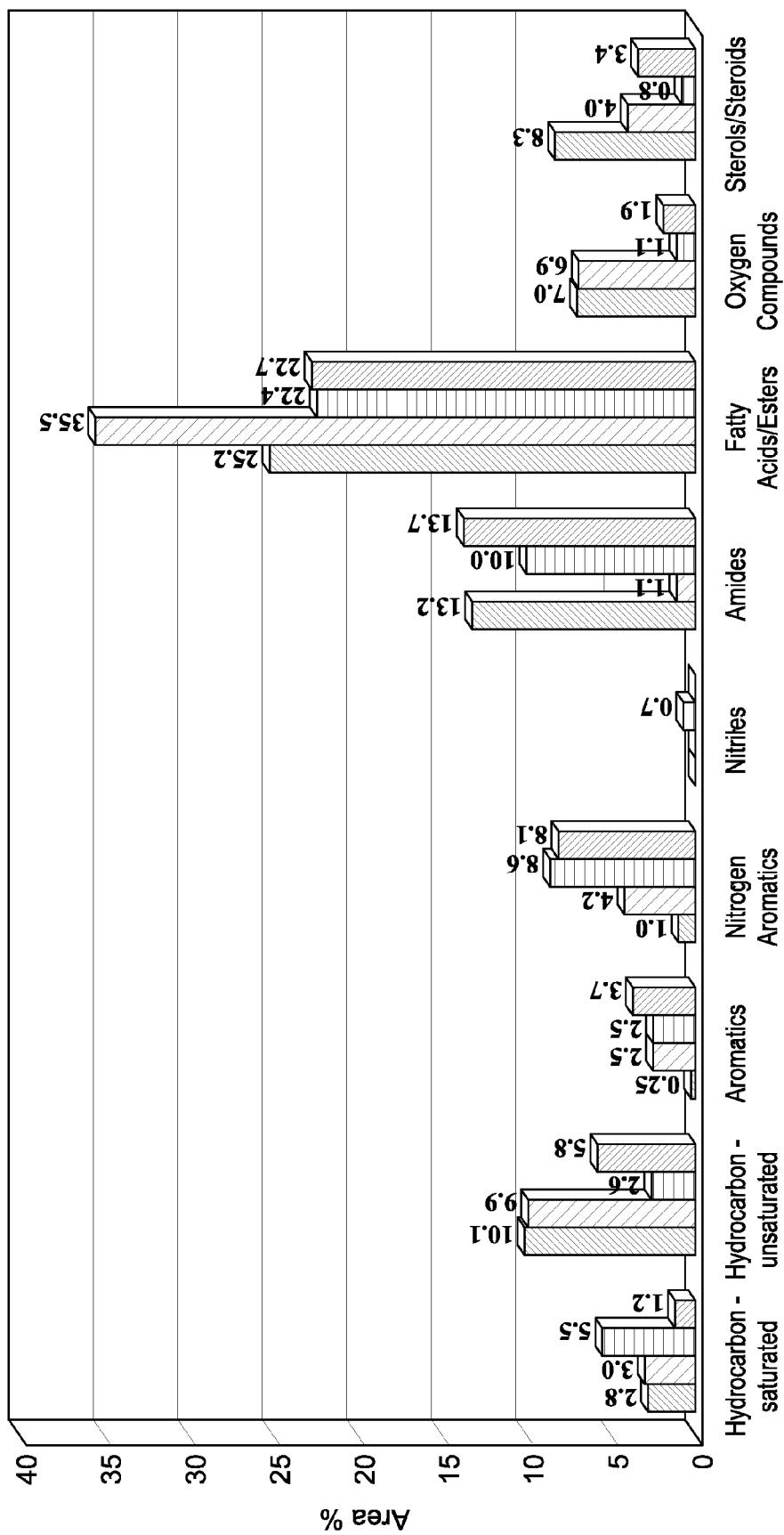
FIG. 8 compares compound classes, from HT GC-MS analysis, of the EXAMPLE III algae oils (from left to right, *Nannochloropsis, Scenedesmus, Spirulina*, and *Dunaliella*) that were hydrothermally treated and extracted with mixed heptanes as a solvent, wherein the x-axis shows various compound classes and the y-axis is area %.
Figure 9:
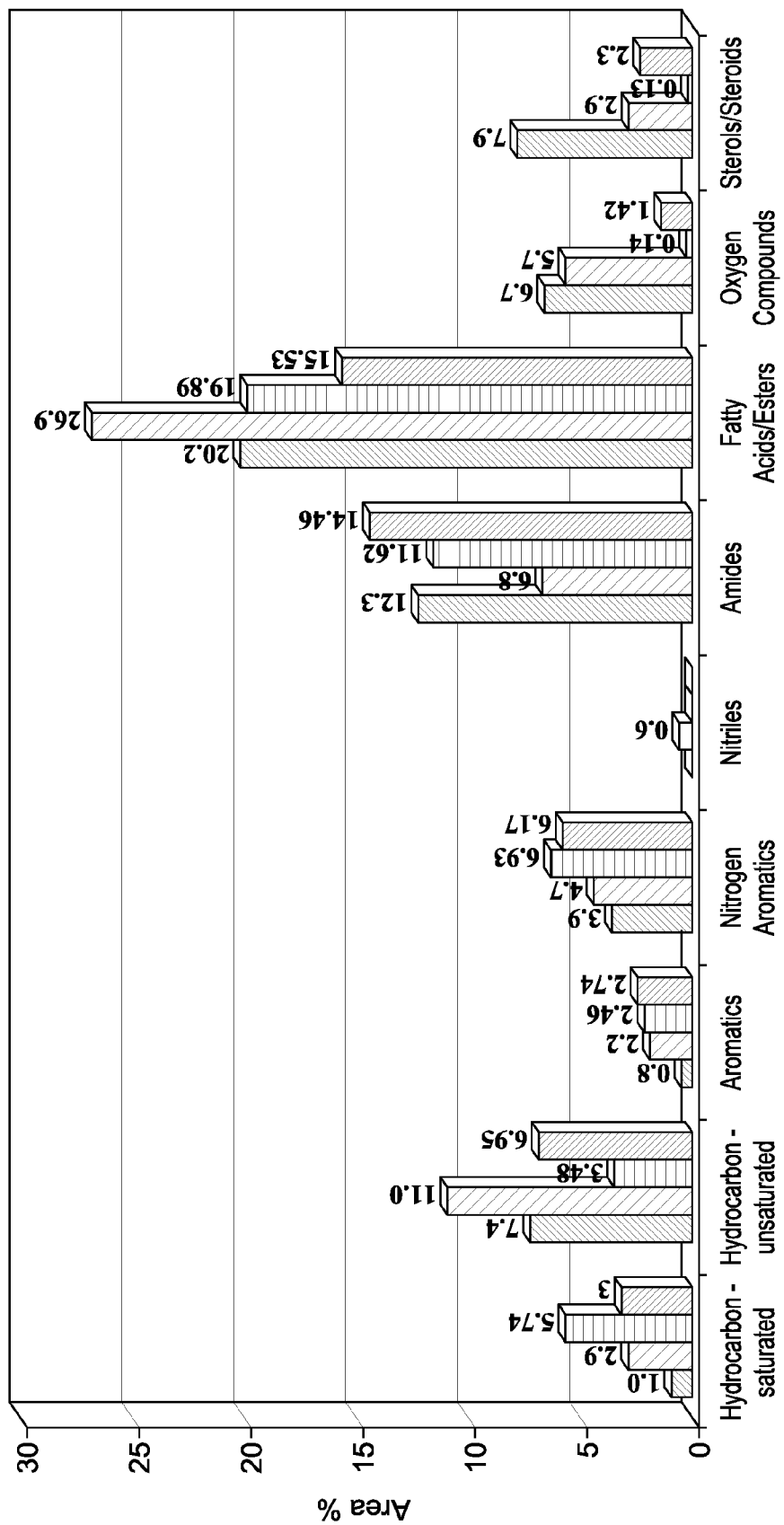
FIG. 9 compares compound classes, from HT GC-MS analysis, of the EXAMPLE III algae oils (from left to right, *Nannochloropsis, Scenedesmus, Spirulina*, and *Dunaliella*) that that were hydrothermally treated and extracted with MIBK as a solvent, wherein the x-axis shows compound classes and the y-axis is area percent.
Figure 10:
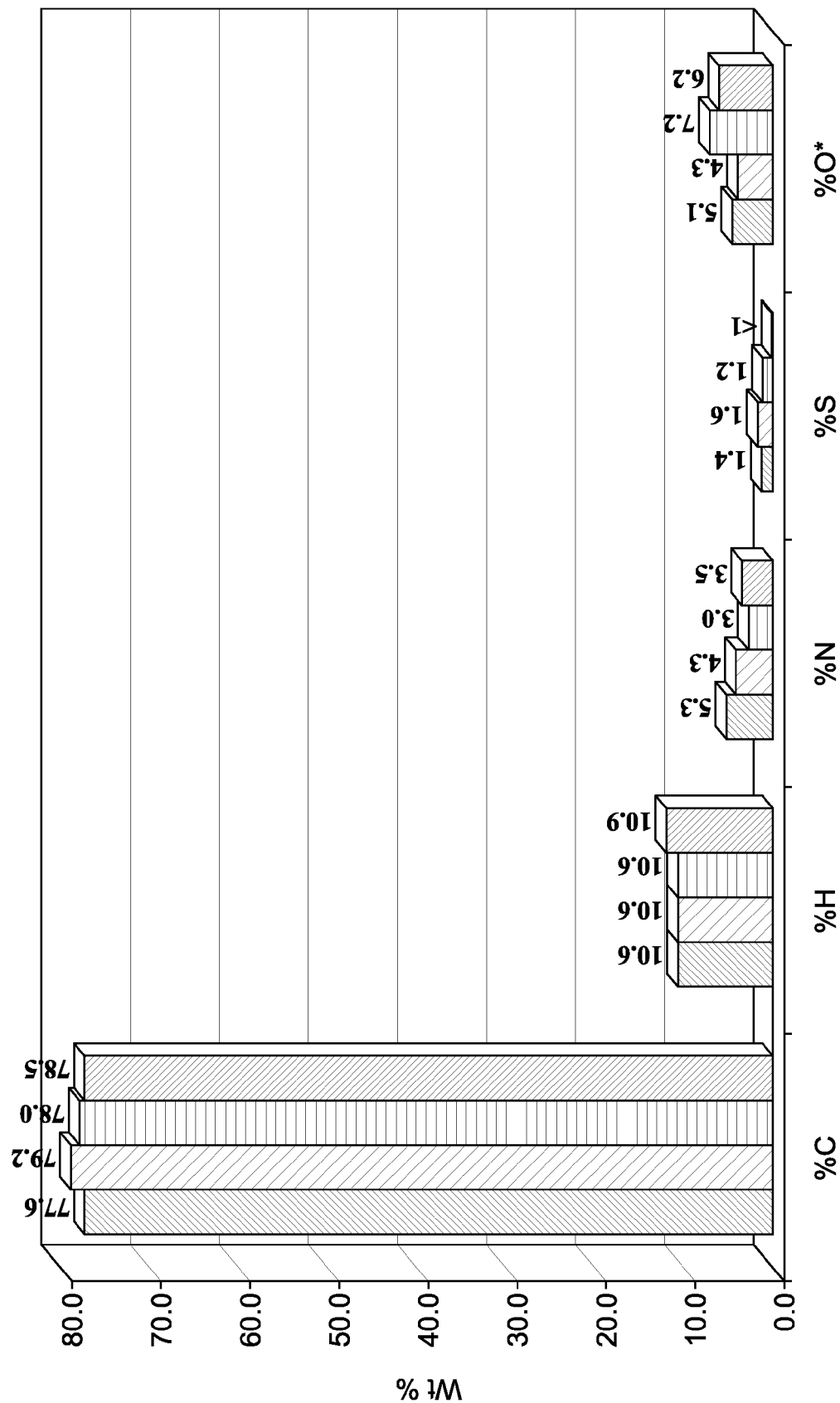
FIG. 10 compares elemental analyses of the algae oils of EXAMPLE III (from left to right, *Spirulina, Dunaliella, Scenedesmus*, and *Nannochloropsis*) that were hydrothermally treated and extracted with mixed heptanes as a solvent, wherein the x-axis shows elements and the y-axis is weight %.
Figure 11:
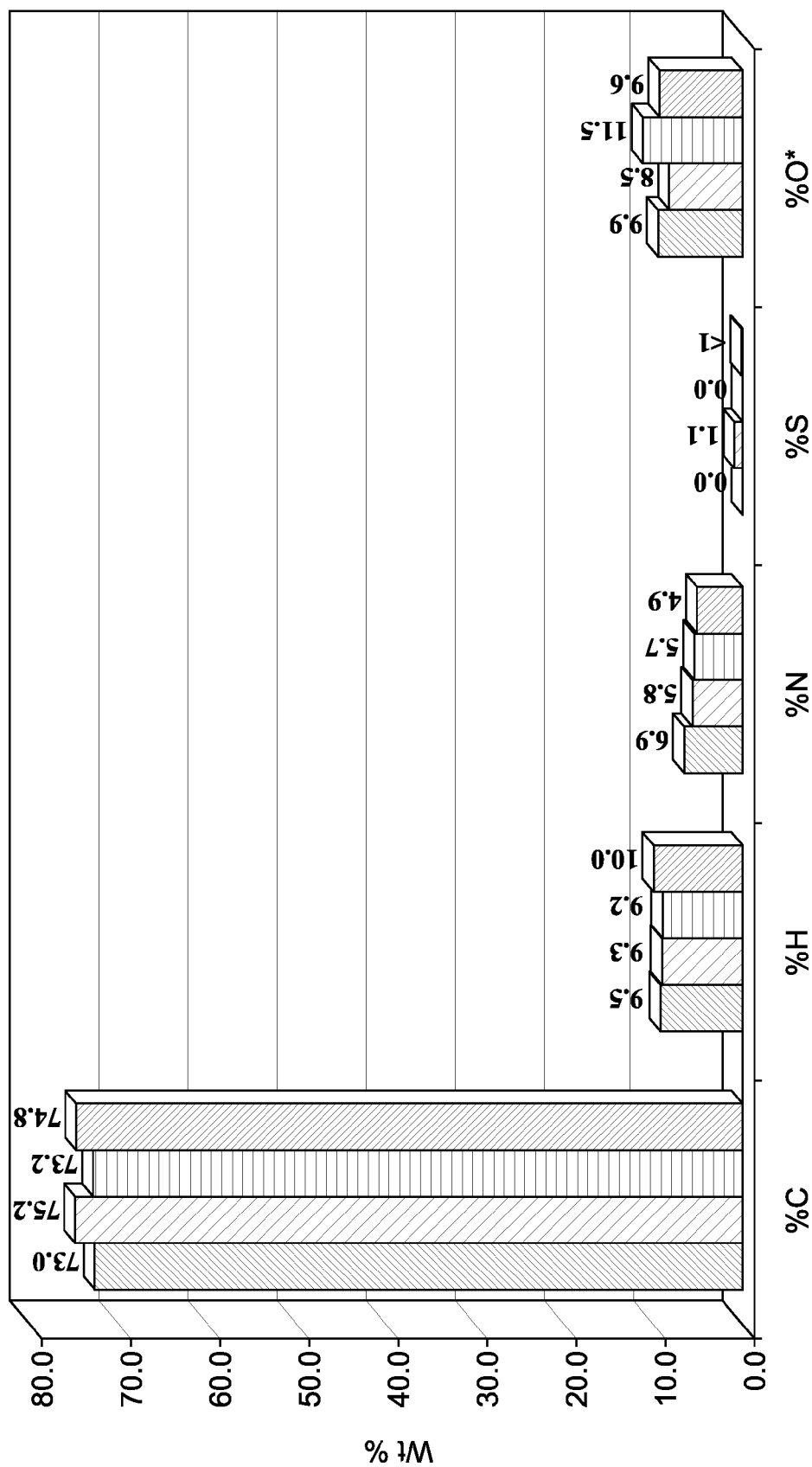
FIG. 11 is a bar-graph of elemental analyses of the algae oils of EXAMPLE III (from left to right, *Spirulina, Dunaliella, Scenedesmus*, and *Nannochloropsis*) that were hydrothermally treated and extracted with MIBK as a solvent, wherein the x-axis shows elements and the y-axis is weight %.
Figure 12:
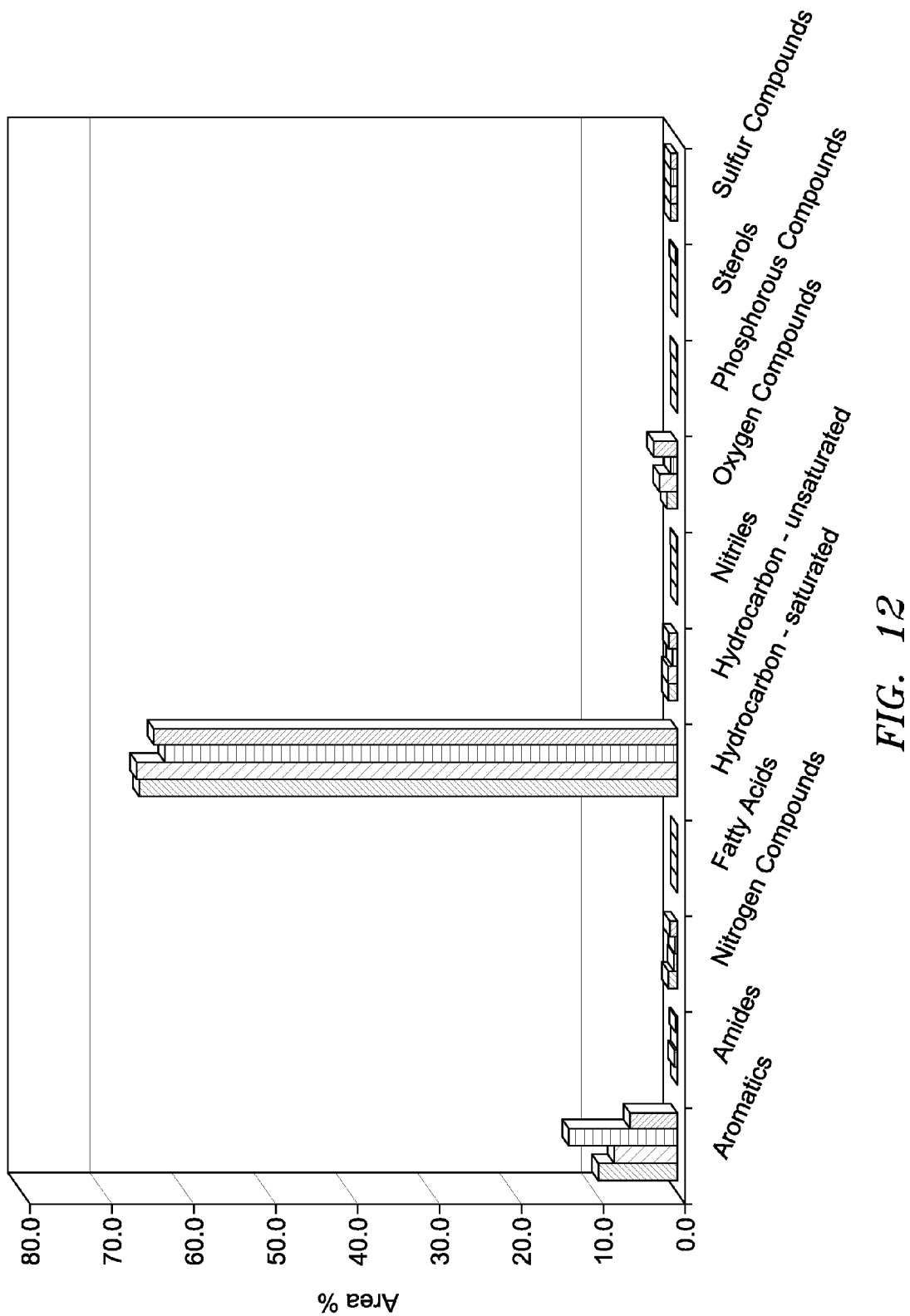
FIG. 12 is a bar-graph of approximate values for compound classes from HT GC-MS of four conventional crude oils, which are from left to right Arabian Light A-55, Arabian Medium Z-11, Arabian Extra-Light B-38, and Arabian Heavy A-49, which are compared to the algae oils of EXAMPLE III in Table 3A-Table 3C, wherein the x-axis shows various compound classes and the y-axis is area %.

FIG. 8 and FIG. 9 portray, in bar-graph form, compound classes by HT GC-MS of algae oil from the four algae strains, extracted with heptanes (FIG. 8) or with MIBK (FIG. 9). FIG. 10 (heptanes extraction) and FIG. 11 (MIBK extraction) portray, in bar-graph form, elemental analysis by HTGC-MS of the same four algae oils.

To provide more perspective regarding the unusual characteristics of the crude algae oils, approximate values relating to some conventional crude oils are added to Table 3A-Table 3D for comparison to the algae oil analyses. These conventional crude oils include four common fossil crude oils, that is, Arabian Light, Arabian Medium, Arabian Extra-Light, and Arabian Heavy, approximate compound classes of which are also graphed in FIG. 12. Two conventional vegetable oils, camelina and canola oil, are also included in Table 3A and Table 3D. Also of interest in Table 3A-Table 3C are the saturated hydrocarbon and aromatics content of typical HVGO (which is a straight-run fraction of fossil crude) and of jet-A fuel (typically a fossil crude kerosene/jet fraction hydrotreated to meet jet-A fuel specifications).

Table 3A-Table 3D and FIG. 4-FIG. 12 show that algae oils produced from multiple strains and solvents are quite similar, but there is a significant difference between the algae oils and the fossil petroleum crudes and the vegetable oils. The algae oils comprise a wide range of compounds, including many fatty acids, unsaturated compounds, nitrogen and oxygen compounds, nitrogen aromatics, amides, and typically (but not from all strains) sterols, and therefore the algae oils are very polar. The petroleum crudes, in comparison, appear to be much "simpler" in that they are nearly entirely comprised of saturated hydrocarbons and aromatics, and are therefore very non-polar. The petroleum crudes have low oxygen and nitrogen content, and typically no fatty acids, but have high sulfur compared to the algae oils. The vegetable oils are substantially entirely TAGs (triacylglycerides, triglycerides).

The elemental analyses of the algae oils of EXAMPLE III may be compared to the algae oil and HVGO in Table 2B, whereby it may be seen that the EXAMPLE III algae oils are similar to the Table 2B algae oil. It may be of interest to also compare the algae oil elemental analyses to that of jet-A fuel, but it should be noted that the hydrogen content and low nitrogen and sulfur content of the jet-A may be partially a result of hydrotreatment of straight-run jet/kerosene fractions to obtain the jet-A fuel.

Example IV

The effect of multiple extraction "passes" on the algae oil composition has been tested, showing the composition, in effect, of multiple crude algae oils obtained sequentially from the same biomass. The individual crude algae oils obtained from each of multiple extraction passes, either individually or in various blends, are also included as embodiments of the disclosure.

In the multiple-pass experiments, algae oil was extracted from *Nannochloropsis* strain biomass, using a 0.5 hour extraction time at 120 degrees C for each pass. "Multiple passes" means repeated solvent additions to the aqueous phase, with the steps of separating the organic phase from aqueous phase and removing solvent from the organic phase (to obtain additional oleaginous compositions) performed between each of the repeated solvent additions. Each addition of solvent followed by separation of phases and solvent removal from the algae oil, may be described as a pass.

Figure 13:
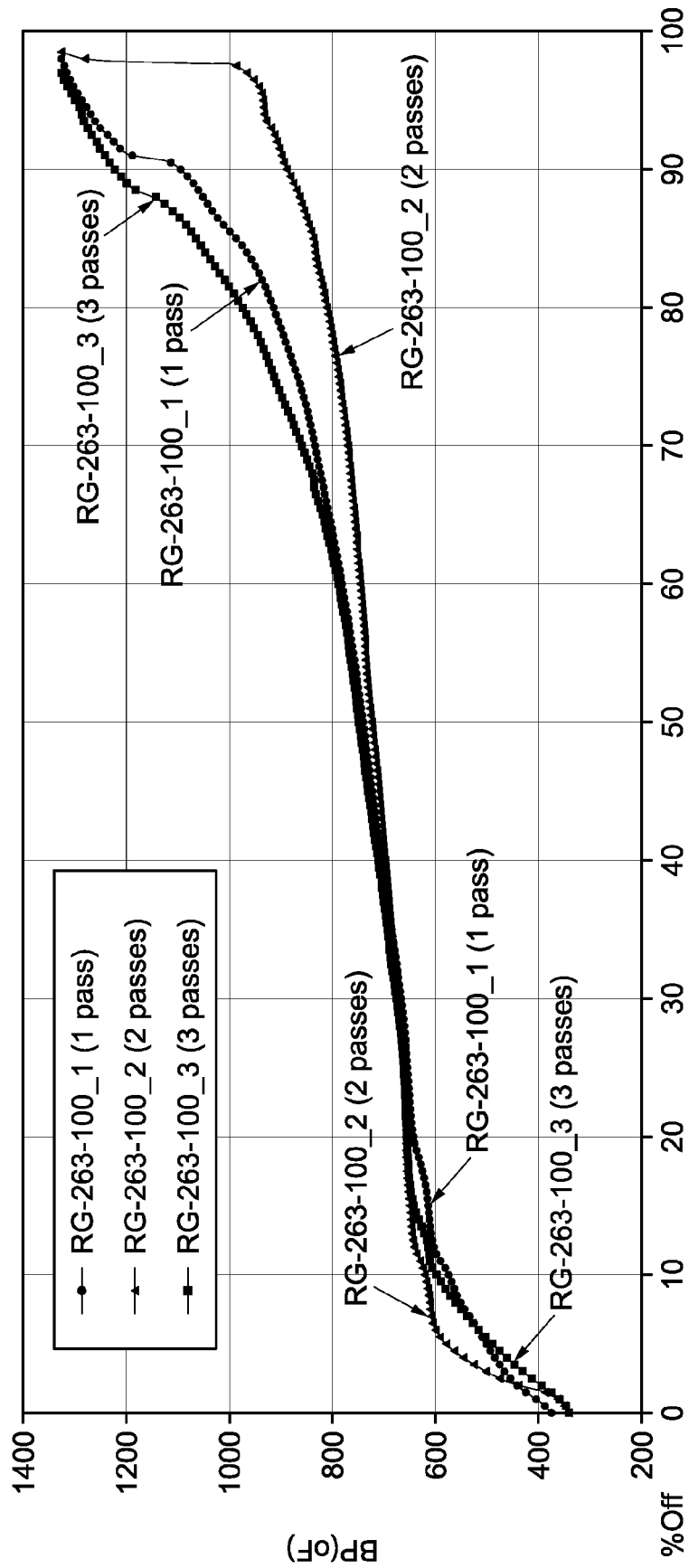
FIG. 13 is an overlay graph of boiling point curves for three algae oils described in EXAMPLE IV according to some embodiments of the disclosure, wherein each algae oil was obtained from a different solvent pass after hydrothermal treatment. The x-axis represents % Off (percent boiled) and the y-axis represents boiling point degrees F.
Figure 14:
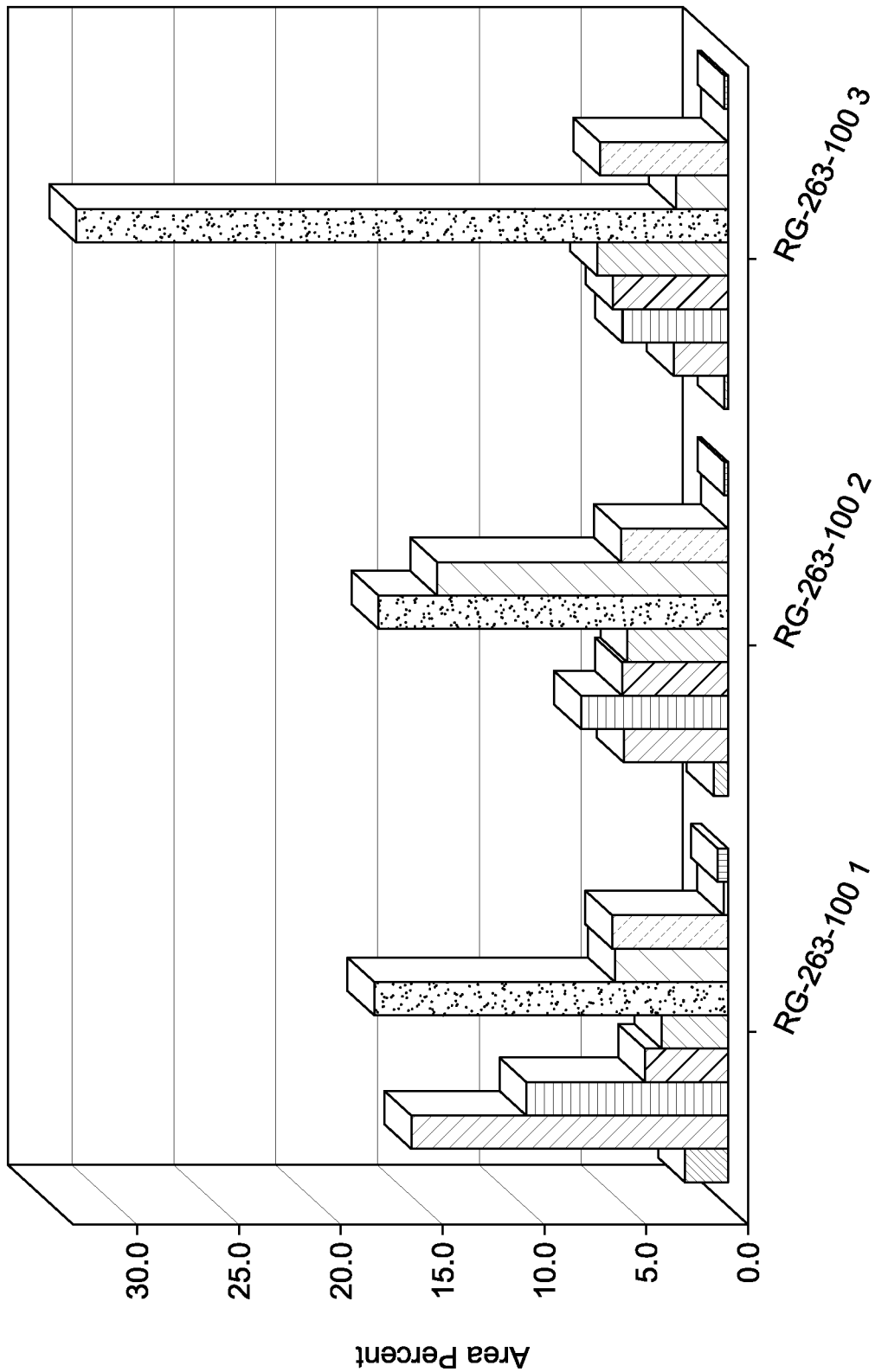
FIG. 14 is a bar-graph of compound classes of the three algae oils of FIG. 13 obtained by HT GC-MS analysis, wherein the y-axis is area % and the x-axis lists compound groups, which are from left to right: saturated hydrocarbons, unsaturated hydrocarbons, sterols, aromatics, nitrogen aromatics, fatty acids, oxygen compounds, amides, nitriles, and fatty acid methyl esters.

FIG. 13 illustrates the boiling curves of the three algae oils obtained from each of the three passes. Table 4 shows elemental analysis of the algae oil from each of the three passes. Table 5 shows compositional analysis of the algae oil from each of the three passes, and FIG. 14 shows the compositional analysis in bar-graph form. From Table 5, one may calculate H/C molar ratios, which are 1.688, 1.648, and 1.639, for the first, second and third passes, respectively; thus, one may see that the H/C molar ratio declines slightly with successive passes, but the ratios remain above 1.6. The composition detailed by GC in Table 5 and FIG. 14 are generally consistent with the compositions of the other algae oils detailed in this Detailed Description, but it is noteworthy that the peak % of each of saturated hydrocarbons, unsaturated hydrocarbon, and sterols declined in successive passes. Area % of oxygen compounds was highest in the second pass. Area % of fatty acids (including esters) was above 15% in each of the algae oils, with fatty acids-esters in the algae oils of the first and second passes being very similar, but fatty acids-esters in the third pass almost doubling. Table 4 and Table 5 are provided below.

TABLE 4

| Elemental Analysis | RG-263-100 1 (1 pass) | RG-263-100 2 (2 passes) | RG-263-100 3 (3 passes) |
| --- | --- | --- | --- |
| Carbon, weight percent | 78.9 | 77.2 | 76.9 |
| Hydrogen, weight percent | 11.1 | 10.6 | 10.5 |
| Nitrogen, weight percent | 5.0 | 6.3 | 5.0 |
| Oxygen, weight percent (by difference) | 4.3 | 5.4 | 7.0 |
| Sulfur, weight percent | 0.7 | 0.4 | 0.6 |
| Hydrogen/Carbon mole ratio | 1.69 | 1.65 | 1.64 |

TABLE 5

| | RG-263-100 1 $1^{st}$ pass | RG-263-100 2 $2^{nd}$ pass | RG-263-100 3 $3^{rd}$ pass |
| --- | --- | --- | --- |
| compound classes, area percent by HT GC-MS | | | |
| hydrocarbon-saturated | 2.1 | 0.7 | 0.2 |
| hydrocarbon-unsaturated | 15.6 | 5.1 | 2.7 |
| aromatics | 4.1 | 5.3 | 5.7 |
| nitrogen aromatics | 3.3 | 4.9 | 6.4 |
| amides | 5.8 | 5.2 | 6.4 |
| nitriles | 0.2 | 0.0 | 0.0 |
| fatty acid | 17.4 | 17.3 | 32.2 |
| fatty acid methyl ester | 0.5 | 0.2 | 0.2 |
| oxygen compounds | 5.6 | 14.3 | 2.6 |
| sterols | 10.0 | 7.3 | 5.2 |
| sulfur compounds | 0.0 | 0.0 | 0.0 |
| unknowns | 35.3 | 39.7 | 38.5 |
| total = | 100.0 | 100.0 | 100.0 |

It may be understood, from this Example and the Claims, that embodiments of the disclosure may include one or more oleaginous compositions from one or more extraction passes from algae biomass, or including two or more blended fractions thereof. Full-boiling-range algae oil can be the entire oleaginous composition resulting from a single solvent pass of any of the hydrothermal extraction methods detailed earlier in this document. When multiple passes are performed, each will typically be full-boiling-range algae oil. It is envisioned, however, that any of these full-boiling-range algae oils may be distilled to obtain one or more especially-desired fractions, and embodiments of the disclosure may be individual fractions of a full-boiling-range algae oil, or selected fractions blended together.

While certain embodiments have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. An algal oil extracted from biomass comprising a non-vascular photosynthetic organism, made by a method comprising:
   a) providing an aqueous composition comprising the biomass and water;
   b) hydrothermally treating the aqueous composition biomass at a temperature from about 260 degrees Celsius to about 300 degrees Celsius, and holding the temperature from zero to about 240 minutes;
   c) cooling the hydrothermally-treated composition to a temperature between ambient temperature and about 150 degrees C.;
   d) performing acid hydrolysis by acidifying the cooled composition; and
   e) extracting the algal oil from the acidified composition; wherein the algal oil is characterized by HT GC-MS to comprise: an area percent of saturated hydrocarbons from about 1.2 to about 3.0; an area percent of aromatics from about 2.5 to about 3.7; an area percent of Nitrogen compounds from about 4.2 to about 8.1; and an area percent of Oxygen compounds from about 1.9 to about 6.9.

2. The algal oil of claim 1, wherein the non-vascular photosynthetic organism is a microalga, a *Dunaliella* species, a *Scenedesmus* species, or a *Spirulina* species.

3. The algal oil of claim 1, wherein
   the algal oil has not been subjected to one or more of hydrotreating, decarboxylation; decarbonylation, hydrodeoxygenation, isomerization (including hydroisomerization), desulfurization, denitrogenation, hydrocracking, and catalytic cracking.

4. The composition of claim 1, wherein said extraction is solvent extraction using one or more solvents selected from the group consisting of:
   hexane, heptane, cyclohexane, toluene (methylbenzene), chloroform (trichloromethane), methyl isobutyl ketone (MIBK), acetonitrile, ethanol, methyl-t-butyl ether (MTBE), methyl ethyl ketone (MEK), propanol, isopropyl alcohol (IPA), methanol, or methylene chloride (dichloromethane),
   a polar solvent, a non-polar solvent, and a combination of a polar and a non-polar solvent.

5. The algal oil of claim 1, wherein the hydrothermal treatment is done without using a catalyst.

6. The algal oil of claim 1, wherein the temperature of said hydrothermal treatment is about 300 degrees Celsius and the hold time is about 30 minutes.

7. The algal oil of claim 1, wherein the biomass is substantially photosynthetic algae.

8. An algal oil extracted from biomass comprising a non-vascular photosynthetic organism, made by a method comprising:
 a) providing an aqueous composition comprising the biomass and water;
 b) hydrothermally treating the aqueous composition at a temperature from about 260 degrees Celsius to about 300 degrees Celsius, and holding the temperature from zero to about 240 minutes;
 c) cooling the hydrothermally-treated composition to a temperature between ambient temperature and about 150 degrees C.;
 d) performing acid hydrolysis by acidifying the cooled composition; and
 e) extracting the algal oil from the acidified composition;
 wherein the algal oil is characterized by HT GC-MS as containing an area percent of saturated hydrocarbons from about 1.2 to about 3.0.

9. The algal oil of claim 8 containing from about 77.6 to about 78.0 weight percent carbon, and about 10.2 to about 10.6 weight percent hydrogen, with a hydrogen to carbon molar ratio above 1.6;
 about 3.0 to about 5.3 weight percent Nitrogen;
 about 1.2 to about 1.4 weight percent Sulfur; and
 about 5.1 to about 7.2 weight percent Oxygen; and
 the algal oil being further characterized by HT CC-MS as containing an area percent of fatty acids and/or fatty acid esters from about 22.7 to about 35.5, an area percent of sterols and/or steroids from about 3.4 to about 4.0, and an area percent of amides from about 1.1 to about 13.7.

10. The algal oil of claim 8, wherein the non-vascular photosynthetic organism is a microalga, a *Dunaliella* species, a *Scenedesmus* species, or a *Spirulina* species.

11. The algal oil of claim 8, wherein the algal oil has not been subjected to one or more of hydrotreating, decarboxylation, decarbonylation, hydrodeoxygenation, isomerization (including hydroisomerization), desulfurization, denitrogenation, hydrocracking, and catalytic cracking.

12. The composition of claim 8, wherein said extraction is solvent extraction using one or more solvents selected from the group consisting of:
 hexane, heptane, cyclohexane, toluene (methylbenzene), chloroform (trichloromethane), methyl isobutyl ketone (MIBK), acetonitrile, ethanol, methyl-t-butyl ether (MTBE), methyl ethyl ketone (MEK), propanol, isopropyl alcohol (IPA), methanol, or methylene chloride (dichloromethane), a polar solvent, a non-polar solvent, and a combination of a polar and a non-polar solvent.

13. The algal oil of claim 8, wherein the hydrothermal treatment is done without using a catalyst.

14. The algal oil of claim 8, wherein the temperature of said hydrothermal treatment is about 300 degrees Celsius and the hold time is about 30 minutes.

15. The algal of claim 8, wherein the biomass is substantially photosynthetic algae.

\* \* \* \* \*